United States Patent
Oh et al.

(10) Patent No.: US 8,877,696 B2
(45) Date of Patent: Nov. 4, 2014

(54) CLEANING COMPOSITIONS COMPRISING PH-SWITCHABLE AMINE SURFACTANTS

(71) Applicant: The Proctor & Gamble Company, Cincinnati, OH (US)

(72) Inventors: Hiroshi Oh, Cincinnati, OH (US); John August Wos, Maineville, OH (US); Robb Richard Gardner, Cincinnati, OH (US); Timothy Bates, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 42 days.

(21) Appl. No.: 13/850,321

(22) Filed: Mar. 26, 2013

(65) Prior Publication Data

US 2013/0252869 A1 Sep. 26, 2013

Related U.S. Application Data

(60) Provisional application No. 61/615,538, filed on Mar. 26, 2012.

(51) Int. Cl.
*C11D 1/62* (2006.01)
*C11D 9/04* (2006.01)

(52) U.S. Cl.
USPC ........... 510/153; 510/130; 510/141; 510/152; 510/292; 510/329; 510/340; 510/343; 510/353; 510/399; 510/437; 510/439; 510/447; 510/481; 510/499; 510/504

(58) Field of Classification Search
USPC ......... 510/130, 141, 152, 153, 329, 340, 343, 510/353, 399, 437, 439, 447, 481, 499, 504, 510/292

See application file for complete search history.

(56) References Cited

U.S. PATENT DOCUMENTS 5,068,431 A 11/1991 Karalis et al.

FOREIGN PATENT DOCUMENTS

| EP | 15032 | * | 9/1980 |
| EP | 0015032 A1 | | 9/1980 |
| WO | 9605280 A1 | | 2/1996 |

* cited by examiner

*Primary Examiner* — Charles Boyer
(74) *Attorney, Agent, or Firm* — Jason J Camp; Melissa G Krasovec

(57) ABSTRACT

A cleaning composition may comprise a pH-switchable sudsing system and a cleansing system. The pH-switchable sudsing system may comprise a primary sudsing agent in combination with a pH-switchable co-surfactant. The pH-switchable co-surfactant is selected from diamine molecules having a general formula $R^1R^2$—N—$R^3$—$N^+(CH_3)_3 X^-$, where $R^1$ is a linear or branched $C_8$ to $C_{16}$ hydrocarbyl, $R^2$ is a linear or branched $C_1$ to $C_3$ hydrocarbyl, $R^3$ is a linear or branched $C_3$ to $C_6$ hydrocarbylene, and X is a counteranion. The tertiary amine nitrogen of the pH-switchable co-surfactant has a $pK_a$ value. When the tertiary amine nitrogen is unprotonated, the pH-switchable co-surfactant may provide a suds-boosting effect in washing solutions at a washing pH above the $pK_a$. When the tertiary amine nitrogen is protonated, the pH-switchable co-surfactant may provide a suds-reducing benefit in rinse waters at a rinse pH below the $pK_a$.

20 Claims, No Drawings

CLEANING COMPOSITIONS COMPRISING PH-SWITCHABLE AMINE SURFACTANTS

TECHNICAL FIELD

The present disclosure relates generally to cleaning compositions and, more particularly, to cleaning compositions that contain a pH-switchable co-surfactant that changes the sudsing characteristics of the cleaning composition based on the pH of an aqueous solution in which the cleaning composition is used.

BACKGROUND

Cleaning compositions for cleaning fabrics such as clothing, for hand-cleaning dishes, or for washing body parts, commonly contain sudsing ingredients such as surfactants or free fatty acids. Especially during washing of clothes and fabrics, dishes, and body parts, where the user is very involved with the washing process, a large volume of suds is initially desirable, because it indicates to the user that sufficient surfactant is present and is performing the desired cleaning.

Though a large volume of suds may be desirable during cleaning, it paradoxically typically takes from 3 to 6 rinses to remove suds to the satisfaction of the person washing. This can add up to a great amount of water being used every day for rinsing around the world—typically about 5 to 10 tons of water per year per household in countries such as India and China, where hand-washing of laundry is standard practice. Because water is often a limited resource, especially in hand washing countries, the use of water for rinsing reduces the amount available for other possible uses such as irrigation, drinking and bathing. Depending on the location and the local practice, there may also be an added energy or labor cost involved with rinsing so many times and with so much water.

Suds suppressors are well-known in, for example, automatic dishwashing detergents and laundry detergents for front-loading washing machines. But when consumers who are accustomed to seeing suds during the wash, an absence of suds leads the consumer to believe that the cleaning composition is not performing to expectations. Because typical suds suppressors do not distinguish between the wash and rinse conditions, they do not solve the problem of providing suds during use while still reducing the need for rinsing.

During rinsing, the typical user of laundry detergents, hand dishwashing detergents, and personal bar soaps typically believes that if suds are still present, then what is being washed is not yet "clean" until the suds are not seen in the rinse. However, it has been found that fewer rinses can sufficiently remove sudsing ingredients such as surfactants. As such, if consumer perception can be overcome in this regard, use of water for rinsing can be reduced with little or no adverse effects to the typical user of the cleaning composition.

Accordingly, because in many countries water and other resources are becoming ever more scarce, the need exists for an effective way to reduce the amount of water used for rinsing of laundry, dishes, and body parts without sacrificing cleaning efficiency and effectiveness. The inventors have discovered that some or all of the above mentioned needs can be at least partially fulfilled through cleaning compositions according to embodiments described below, in which a pH-switchable co-surfactant is present.

SUMMARY

In some embodiments, a cleaning composition may comprise a pH-switchable sudsing system and a cleansing system. The pH-switchable sudsing system may comprise a primary sudsing agent such as a sudsing surfactant and/or a free fatty acid, in combination with a pH-switchable co-surfactant. The pH-switchable co-surfactant is selected from diamine molecules comprising a quaternary amine and a tertiary amine, according to a structure described below in detail. The tertiary amine of the pH-switchable co-surfactant has a $pK_a$ value, a protonated form, and a deprotonated form. The deprotonated form of the pH-switchable co-surfactant may provide a suds-boosting effect in washing solutions at a washing pH above the $pK_a$ of the pH-switchable co-surfactant. The protonated form of the pH-switchable co-surfactant may provide a suds-reducing benefit in rinse waters at a rinse pH below the $pK_a$ of the pH-switchable co-surfactant.

In further embodiments, methods for hand-washing a fabric using the cleaning compositions are described. Such methods may include, for example, first diluting a cleaning composition according embodiments described herein in water at a weight ratio of water to the cleaning composition of from about 1:150 to about 1:1000 to form a laundry liquor having a pH. As noted above, the pH-switchable co-surfactant of the cleaning composition has a $pK_a$. The methods may further include hand washing a fabric in the laundry liquor and maintaining pH of the laundry liquor above the $pK_a$ of the pH-switchable co-surfactant during the washing. The method may further include rinsing the fabric in a rinse bath having a pH less than the $pK_a$ of the pH-switchable co-surfactant.

These and other features, aspects, and advantages of the embodiments herein will become better understood with reference to the following description and appended claims.

DETAILED DESCRIPTION

It is to be understood that both the foregoing background and the following detailed description describe various embodiments and are intended to provide an overview or framework for understanding the nature and character of the claimed subject matter.

Reference will now be made to various embodiments of cleaning compositions having sudsing benefits with regard to the pH of an aqueous solution in which the cleaning compositions are used. The cleaning compositions may comprise a pH-switchable sudsing system and a cleansing system. The pH-switchable sudsing system may comprise a primary sudsing agent and a pH-switchable co-surfactant. In some embodiments, the primary sudsing agent may comprise a surfactant, a free fatty acid, or both. The pH-switchable co-surfactant may be selected from a class of amines described in detail below. The cleansing system may comprise one or more appropriate ingredients for formulating the pH-switchable sudsing system into cleaning compositions such as laundry detergents, hand-dishwashing detergents, or bar soaps, for example. In some embodiments, the combination of the pH-switchable co-surfactant and the primary sudsing agent may provide benefits to the cleaning compositions such as a boosting of suds at a typical washing pH, a reduction or elimination of suds at a rinsing pH lower than the washing pH, or both.

Cleaning compositions according to several embodiments may comprise a pH-switchable sudsing system and a cleansing system. In non-limiting illustrative embodiments, the cleaning compositions may comprise, based on the total weight of the cleaning composition, from about 0.01 wt. % to about 70 wt. %, or from about 0.1 wt. % to about 70 wt. %, or from about 1 wt. % to about 70 wt. %, or from about 5 wt. % to about 70 wt. %, or from about 10 wt. % to about 60 wt. %, or from about 20 wt. % to about 50 wt. %, or from about 30 wt. % to about 50 wt. %, of the pH-switchable sudsing system. In non-limiting illustrative embodiments the cleaning compositions may comprise, based on the total weight of the cleaning composition, from about 0.0001 wt. % to about 99.99 wt. %, or from about 0.0001 wt. % to about 99 wt. %, or from about 0.0001 wt. % to about 95 wt. %, or from about 0.0001 wt. % to about 90 wt. %, or from about 0.0001 wt. % to about 80 wt. %, or from about 0.0001 wt. % to about 70 wt. % of the cleansing system. For example, the cleaning compositions may comprise from about 0.01 wt. % to about 70 wt. % of the pH-switchable sudsing system and from about 0.0001 wt. % to about 99.99 wt. % of the cleansing system, based on the total weight of the cleaning composition.

pH-Switchable Sudsing System

According to various embodiments, the pH-swtichable sudsing system of the cleaning composition may comprise a primary sudsing agent and a pH-switchable co-surfactant. In illustrative embodiments, the pH-switchable sudsing system may comprise, based on the total weight of the pH-switchable sudsing system, from about 0.05 wt. % to 99.99 wt. %, or from about 0.5 wt. % to 99.99 wt. %, or from about 1 wt. % to 99.99 wt. %, or from about 5 wt. % to 99.99 wt. %, or from about 10 wt. % to 99.99 wt. %, or from about 25 wt. % to 99.99 wt. %, from about 50 wt. % to 99.99 wt. %, or from about 75 wt. % to 99.99 wt. %, or from about 90 wt. % to 99.99 wt. %, or from about 95 wt. % to 99.99 wt. %, or from about 99 wt. % to 99.99 wt. %, or from about 99.95 wt. % to 99.99 wt. %, of the primary sudsing agent. In illustrative embodiments, the pH-switchable sudsing system may comprise, based on the total weight of the pH-switchable sudsing system, from about 0.01 wt. % to about 15 wt. %, or from about 0.5 wt. % to about 15 wt. %, or from about 1 wt. % to about 15 wt. %, or from about 5 wt. % to about 15 wt. %, or from about 10 wt. % to about 15 wt. %, or from about 0.01 wt. % to about 10 wt. %, from about 0.5 wt. % to about 10 wt. %, or from about 1 wt. % to about 10 wt. %, or from about 5 wt. % to about 10 wt. %, of the pH-switchable co-surfactant. In some embodiments, the weight ratio of the primary sudsing agent to the pH-switchable co-surfactant in the cleaning composition may be from about 6:1 to about 50:1 or from about 10:1 to about 20:1.

Primary Sudsing Agent

The primary sudsing agent in the pH-switchable sudsing system of the cleaning composition preferably is selected based on the intended application or formulation for the cleaning composition. For example, in some embodiments the cleaning composition may be used as a laundry detergent, whereas in other embodiments the cleaning composition may be used as a hand-dishwashing detergent or a bar soap. In embodiments of the cleaning composition, wherein the cleaning composition is formulated as a laundry detergent or a hand-dishwashing detergent, the primary sudsing agent preferably may be selected from sudsing surfactants such as anionic surfactants, nonionic surfactants, amphoteric surfactants, zwitterionic surfactants, and combinations thereof. In embodiments of the cleaning composition, wherein the cleaning composition is formulated into a bar soap, for example, the primary sudsing agent preferably comprises a free fatty acid and may further comprise one or more sudsing surfactants such as anionic surfactants, nonionic surfactants, amphoteric surfactants, zwitterionic surfactants, and combinations thereof.

Sudsing surfactants useful herein typically function as the workhorse surfactant of the cleaning composition, removing dirt and soils from laundry or dishes and forming voluminous, and/or resilient suds during normal use. Thus, the sudsing surfactant typically has a sudsing profile of at least about 5 cm, or from about 8 cm to 25 cm, as measured by the below Suds Testing Protocol herein. Because consumers continue to desire to see some suds on the surface of washing solutions such as laundry liquors, it is beneficial to provide a sudsing surfactant.

In an embodiment herein, the sudsing surfactant comprises an anionic moiety, or multiple anionic moieties. Without intending to be limited by theory, it is believed that an anionic moiety allows the sudsing surfactant to attract the molecules of the pH-switchable co-surfactant, described below, so that the sudsing surfactant is pulled from the suds. This in turn reduces the sudsing surfactant available to maintain suds in the rinse, and initiates a significantly faster suds collapse. In an embodiment herein the sudsing surfactant is selected from the group consisting of anionic surfactants, zwitterionic surfactants, and combinations thereof. In another embodiment, the sudsing surfactant comprises or consists of anionic surfactants. In an embodiment the sudsing surfactant is an anionic surfactant well-known in detergents and has an alkyl chain length of from about 6 carbon atoms ($C_6$), to about 22 carbon atoms ($C_{22}$), or from about $C_{12}$ to about $C_{18}$. Upon physical agitation, anionic surfactants form suds at the air-water interface. Suds indicate to consumers that surfactant is present to release soils, oils, etc. Non-limiting anionic surfactants for use in embodiments described herein include:

a) linear alkyl benzene sulfonates (LAS), or $C_{11}$-$C_{18}$ LAS;

b) primary, branched-chain and random alkyl sulfates (AS), or $C_{10}$-$C_{20}$ AS;

c) secondary (2,3) alkyl sulfates having formulas (I) and (II), or $C_{10}$-$C_{18}$ secondary alkyl sulfates:

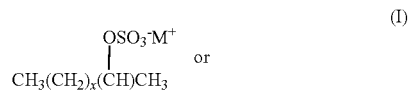

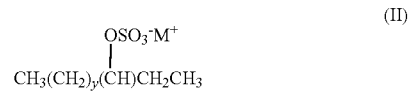

M in formulas (I) and (II) is hydrogen or a cation which provides charge neutrality such as sodium, potassium, and/or ammonium. Above, x is from about 7 to about 19, or about 9 to about 15; and y is from about 8 to about 18, or from about 9 to about 14;

d) alkyl alkoxy sulfates, and alkyl ethoxy sulfates ($AE_xS$), or $C_{10}$-$C_{18}$ $AE_xS$ where x is from about 1 to about 30, or from about 2 to about 10;

e) alkyl alkoxy carboxylates, or $C_6$-$C_{18}$ alkyl alkoxy carboxylates, or those with about 1-5 ethoxy (EO) units;

f) mid-chain branched alkyl sulfates as discussed in U.S. Pat. No. 6,020,303 to Cripe, et al., granted on Feb. 1, 2000; and U.S. Pat. No. 6,060,443 to Cripe, et al., granted on May 9, 2000;

g) mid-chain branched alkyl alkoxy sulfates as discussed in U.S. Pat. No. 6,008,181 to Cripe, et al., granted on Dec. 28, 1999; and U.S. Pat. No. 6,020,303 to Cripe, et al., granted on Feb. 1, 2000;

h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548;

h) methyl ester sulfonate (MES); and i) primary, branched chain and random alkyl or alkenyl carboxylates, or those having from about 6 to about 18 carbon atoms.

In an embodiment herein, the anionic surfactant may contain a mixture of anionic surfactants. The anionic surfactant may be a water-soluble salt, or an alkali metal salt, or a sodium and/or potassium salt.

Suds boosting co-surfactants may also be used to boost suds during the washing procedure. Many such suds boosting co-surfactants are often also anionic surfactants, and are included in the total anionic surfactant above.

Non-limiting examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975, at column 19, line 38 through column 22, line 48, for examples of zwitterionic surfactants; betaine, including alkyl dimethyl betaine and cocodimethyl amidopropyl betaine, $C_8$ to $C_{18}$ (or $C_{12}$ to $C_{18}$) amine oxides and sulfo and hydroxy betaines, such as N-alkyl-N,N-dimethylamino-1-propane sulfonate where the alkyl group can be $C_8$ to $C_{18}$, or $C_{10}$ to $C_{14}$.

The amphoteric surfactant herein is selected from water-soluble amine oxide surfactants, including amine oxides containing one $C_{10-18}$ alkyl moiety and 2 moieties selected from $C_{1-3}$ alkyl groups and $C_{1-3}$ hydroxyalkyl groups; phosphine oxides containing one $C_{10-18}$ alkyl moiety and 2 moieties selected from $C_{1-3}$ alkyl groups and $C_{1-3}$ hydroxyalkyl groups; and sulfoxides containing one $C_{10-18}$ alkyl moiety and a moiety selected from $C_{1-3}$ alkyl and $C_{1-3}$ hydroxyalkyl moieties.

A useful amine oxide surfactant is:

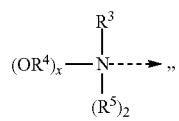

where $R^3$ is a $C_{8-22}$ alkyl, a $C_{8-22}$ hydroxyalkyl, or a $C_{8-22}$ alkyl phenyl group; each $R^4$ is a $C_{2-3}$ alkylene, or a $C_{2-32}$ hydroxyalkylene group; x is from 0 to about 3; and each $R^5$ is a $C_{1-3}$ alkyl, a $C_{1-3}$ hydroxyalkyl, or a polyethylene oxide containing from about 1 to about 3 EOs. The $R^5$ groups may form a ring structure, e.g., through an oxygen or nitrogen atom. The amine oxide surfactant may be a $C_{10-18}$ alkyl dimethyl amine oxide and/or a $C_{8-12}$ alkoxy ethyl dihydroxy ethyl amine oxide.

A useful propyl amine oxide is:

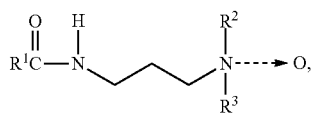

where $R^1$ is a alkyl, 2-hydroxy $C_{8-18}$ alkyl, 3-hydroxy $C_{8-18}$ alkyl, or 3-$C_{8-18}$ alkoxy-2-hydroxypropyl; $R^2$ and $R^3$ are each methyl, ethyl, propyl, isopropyl, 2-hydroxyethyl, 2-hydroxypropyl, or 3-hydroxypropyl and n is from 0 to 10.

Also useful is:

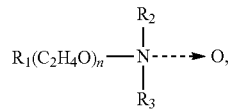

where $R^1$ is a $C_{8-18}$ alkyl, 2-hydroxy $C_{8-18}$ alkyl, 3-hydroxy $C_{8-18}$ alkyl, or 3-$C_{8-18}$ alkoxy-2-hydroxypropyl; and $R^2$, $R^3$ and n are as defined above.

Non-limiting amphoteric surfactants useful herein are known in the art and include amido propyl betaines and derivatives of aliphatic or heterocyclic secondary and ternary amines with a straight chain, or branched aliphatic moiety and wherein one of the aliphatic substituents are $C_{8-24}$ and at least one aliphatic substituent contains an anionic water-soluble group.

In preferred embodiments, particularly those wherein the cleaning composition is a laundry detergent or a hand-dishwashing detergent, the primary sudsing agent comprises at least one anionic surfactant selected from the group consisting of linear alkyl benzene sulfonates, alkyl sulfates, alkyl alkoxylated sulfates, betaines, alkyl amine oxides, and mixtures thereof.

Particularly in embodiments, wherein the cleaning composition is formulated into a personal bar soap, for example, the primary sudsing agent may contain a soap. In some embodiments, the soap may include at least one free fatty acid and, optionally, may further contain at least one of the sudsing surfactants described above. In other embodiments, the soap includes one or more of the sudsing surfactants described above.

In further embodiments, the soap can include a typical soap, i.e., the alkali metal or alkanol ammonium salts of alkane- or alkene monocarboxylic acids. Sodium, magnesium, potassium, calcium, mono-, di- and tri-ethanol ammonium cations, or combinations thereof, are also suitable. Generally, the soap included as the primary sudsing agent herein can include sodium soaps or a combination of sodium soaps with from about 1% to about 25% ammonium, potassium, magnesium, calcium or a mixture of these soaps. According to illustrative embodiments, the soaps useful herein are the well known alkali metal salts of alkanoic or alkenoic acids having about 12 to 22 carbon atoms, preferably about 12 to about 18 carbon atoms or alkali metal carboxylates of alkyl or alkene hydrocarbons having about 12 to about 22 carbon atoms.

The primary sudsing agent also may include soaps having a fatty acid distribution of coconut oil that can provide the lower end of the broad molecular weight range or a fatty acid distribution of peanut or rapeseed oil, or their hydrogenated derivatives, that can provide the upper end of the broad molecular weight range.

For the primary sudsing agent herein, it can be preferred to use soaps that include the fatty acid distribution of tallow and vegetable oil. The tallow can include fatty-acid mixtures that typically have an approximate carbon chain length distribution of 2.5% $C_{14}$, 29% $C_{16}$, 23% $C_{18}$, 2% palmitoleic, 41.5% oleic and 3% linoleic. The tallow can also include other mixtures with similar distribution, such as the fatty acids derived from various animal tallows and lard. According to an example embodiment, the tallow can also be hardened (i.e., hydrogenated) to convert part or all of the unsaturated fatty acid moieties to saturated fatty acid moieties. More preferably, the vegetable oil is selected from the group consisting of palm oil, coconut oil, palm kernel oil, palm oil stearine, and hydrogenated rice bran oil, or mixtures thereof, because these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principal chain lengths are $C_{16}$ and higher.

A preferred soap is sodium soap having a mixture of about 50 wt. % tallow, 30 wt. % palm oil stearine, and 20 wt. % Palm Kernel Oil (PKO) or coconut oil. The soaps may contain unsaturated fatty acid in accordance with commercially acceptable standards. An excessive degree of unsaturation in the soap is normally avoided.

According to illustrative embodiments, the primary sudsing agent may include soaps having unsaturation in accordance with commercially acceptable standards. For example, in one embodiment, the soaps can include unsaturation in the ranges of from about 37% to 45% of the saponified material. In an illustrative embodiment, the soap included in the antimicrobial bar composition can be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids such as lauric ($C_{12}$), myristic ($C_{14}$), palmitic ($C_{16}$), or stearic ($C_{18}$) acids with an alkali metal hydroxide or carbonate.

The primary sudsing agent can also optionally include free fatty acid. Free fatty acids can be incorporated in the cleaning composition, particularly when the cleaning composition is a personal bar soap, to provide enhance skin feel benefits, such as softer and smoother feeling skin. Suitable free fatty acids include, without limitation, tallow, coconut, palm and palm kernel fatty acids. A preferred free fatty acid in the primary sudsing agent is palm kernel fatty acid. Other fatty acids can be employed although the low melting point fatty acids, such as lauric acid, can be preferred for ease of processing. When present, preferred amounts of free fatty acid added as the primary sudsing agent are from about 0.5 wt. % to about 2 wt. %, most preferably from about 0.75 wt. % to about 1.5 wt. %, based on the total weight of the cleaning composition.

In preferred embodiments, particularly in those wherein the cleaning composition is a personal bar soap, the primary sudsing agent comprises at least one free fatty acid. Preferably, the at least one free fatty acid is selected from the group consisting of pure-chain fatty acids, monoglycerides, diglycerides, triglycerides, and fatty acid-containing oils. In further preferred embodiments, particularly in those wherein the cleaning composition is a personal bar soap, the primary sudsing agent, the primary sudsing agent is selected from the group consisting of acyl isethionates, acyl sarcosinates, alkylglycerylether sulfonates, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulfonate, the alkyl ether sulfates, and mixtures thereof.

pH-Switchable Co-Surfactant

As described above, the cleaning compositions further comprise a pH-switchable co-surfactant or a mixture of pH-switchable co-surfactants as a component of the sudsing system. In general, each pH switchable co-surfactant in the cleaning compositions is selected from compounds having formula (I):

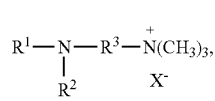

(I)

where: $R^1$ is a linear or branched $C_8$ to $C_{16}$ hydrocarbyl; $R^2$ is a linear or branched $C_1$ to $C_3$ hydrocarbyl; $R^3$ is a linear or branched $C_3$ to $C_6$ hydrocarbylene; and X is a counteranion.

As used herein, the term "hydrocarbyl" refers to a monovalent radical formed by removing any one hydrogen from a hydrocarbon molecule, where a "hydrocarbon molecule" is any molecule consisting of hydrogen atoms and carbon atoms. As used herein, the term "$C_x$ to $C_y$ hydrocarbyl," where x and y are integers, refers to a hydrocarbyl having from x to y total carbon atoms and a sufficient number of hydrogen atoms to maintain the monovalency of the hydrocarbyl.

As used herein, the term "hydrocarbylene" refers to a divalent radical formed by removing any two hydrogen atoms from a hydrocarbon. The two hydrogen atoms may have been removed from the same carbon atom or from two different carbon atoms. As used herein, the term "$C_x$ to $C_y$ hydrocarbylene," where x and y are integers, refers to a hydrocarbylene having from x to y total carbon atoms and a sufficient number of hydrogen atoms to maintain the divalency of the hydrocarbylene.

In the compounds having formula (I), group $R^1$ may be a linear or branched $C_8$ to $C_{16}$ hydrocarbyl, as defined above. In some embodiments, group $R^1$ may be a linear or branched $C_{10}$ to $C_{16}$ hydrocarbyl or a linear or branched $C_{10}$ to $C_{14}$ hydrocarbyl. Typically, the group $R^1$ is a saturated hydrocarbyl containing no double bonds. In preferred embodiments, group $R^1$ may be a linear $C_8$ to $C_{16}$ hydrocarbyl, a linear $C_{10}$ to $C_{16}$ hydrocarbyl, or a linear $C_{10}$ to $C_{14}$ hydrocarbyl. In non-limiting illustrative embodiments, group $R^1$ may be selected from the group consisting of 1-octyl, 1-nonyl, 1-decyl, 1-undecyl, 1-dodecyl, 1-tridecyl, 1-tetradecyl, 1-pentadecyl, and 1-hexadecyl. Preferably, group $R^1$ is selected from 1-octyl, 1-decyl, 1-dodecyl, and 1-tetradecyl. More preferably, group $R^1$ is 1-dodecyl.

In the compounds having formula (I), group $R^2$ may be a linear or branched $C_1$ to $C_3$ hydrocarbyl. In illustrative embodiments, group $R^2$ may be selected from the group consisting of methyl, ethyl, 1-butyl, and 2-butyl. In preferred embodiments, group $R^2$ is methyl. Without intent to be bound by theory, it is believed that selecting group $R^2$ as a hydrocarbyl, as opposed to a hydrogen atom, may decrease intermolecular hydrogen-bond formation between molecules of the pH-switchable co-surfactant, thereby decreasing self-aggregation of the pH-switchable co-surfactant into hydrophobic particles even at high pH typically encountered in an aqueous washing solution. Furthermore, while it is contemplated that group $R^2$ could also be a linear or branched $C_4$ hydrocarbyl such as 1-butyl or 2-butyl (i.e., isobutyl), in preferred embodiments group $R^2$ is the linear or branched $C_1$ to $C_3$ hydrocarbyl, as described above.

In the compounds having formula (I), group $R^3$ may be a linear or branched $C_3$ to $C_6$ hydrocarbylene. In some embodiments, group $R^3$ is a linear $C_3$ to $C_6$ hydrocarbylene such as 1,3-propanediyl, 1,4-butanediyl, 1,5-pentanediyl, or 1,6-hexanediyl, for example. In preferred embodiments, group $R^3$ is selected from the group consisting of 1,3-propanediyl, 1,4-butanediyl, and 1,5-pentanediyl. Most preferably, group $R^3$ is 1,3-propanediyl. Thus, among the pH-switchable co-surfactants selected from compounds or mixtures of compounds each having formula (I), in illustrative embodiments a particularly preferable compound is a compound comprising a 3-(dodecyl(methyl)amino)-N,N,N-trimethylpropan-1-aminium(1+) cation (in which $R^1$ is dodecyl, $R^2$ is methyl, $R^3$ is 1,3-propanediyl, charge-balanced by a counteranion X, described below.

Non-limiting, illustrative embodiments of the cationic portions of pH-switchable co-surfactants suitable for use in the pH-switchable sudsing system of the cleaning compositions herein (when charge-balanced with a counteranion X) are listed below in TABLE 1. Though the compounds in TABLE 1 having $R^2$ as a hydrogen atom (—H) or isobutyl (—CH$_2$CH(CH$_3$)$_2$) are not preferred examples of the pH-switchable co-surfactants described herein and may have fewer benefits to the cleaning compositions, it is contemplated that each compound in which $R^2$ is hydrogen or isobutyl may be used in place of the compounds in which $R^2$ is a linear or branched $C_1$ to $C_3$ hydrocarbyl, as described above.

TABLE 1

$$R^1-\underset{\underset{R^2}{|}}{N}-R^3-\overset{+}{N}(CH_3)_3$$

| Number | $R^1$ | $R^2$ | $R^3$ | Cationic Portion Name |
|---|---|---|---|---|
| 1 | —(CH$_2$)$_7$CH$_3$ | —CH$_3$ | —(CH$_2$)$_3$— | 3-(methyl(octyl)amino)-N,N,N-trimethylpropan-1-aminium(1+) |
| 2 | —(CH$_2$)$_9$CH$_3$ | —CH$_3$ | —(CH$_2$)$_3$— | 3-(decyl(methyl)amino)-N,N,N-trimethylpropan-1-aminium(1+) |
| 3 | —(CH$_2$)$_{11}$CH$_3$ | —CH$_3$ | —(CH$_2$)$_3$— | 3-(dodecyl(methyl)amino)-N,N,N-trimethylpropan-1-aminium(1+) |
| 4 | —(CH$_2$)$_{13}$CH$_3$ | —CH$_3$ | —(CH$_2$)$_3$— | 3-(methyl(tetradecyl)amino)-N,N,N-trimethylpropan-1-aminium(1+) |
| 5 | —(CH$_2$)$_{11}$CH$_3$ | —(CH$_2$)$_2$CH$_3$ | —(CH$_2$)$_3$— | 3-(dodecyl(propyl)amino)-N,N,N-trimethylpropan-1-aminium(1+) |
| 6 | —(CH$_2$)$_{11}$CH$_3$ | —CH$_2$CH(CH$_3$)$_2$ | —(CH$_2$)$_3$— | 3-(dodecyl(isobutyl)amino)-N,N,N-trimethylpropan-1-aminium(1+) |
| 7 | —(CH$_2$)$_7$CH$_3$ | —CH$_3$ | —(CH$_2$)$_4$— | 4-(methyl(octyl)amino)-N,N,N-trimethylbutan-1-aminium(1+) |
| 8 | —(CH$_2$)$_9$CH$_3$ | —CH$_3$ | —(CH$_2$)$_4$— | 4-(decyl(methyl)amino)-N,N,N-trimethylbutan-1-aminium(1+) |
| 9 | —(CH$_2$)$_{11}$CH$_3$ | —CH$_3$ | —(CH$_2$)$_4$— | 4-(dodecyl(methyl)amino)-N,N,N-trimethylbutan-1-aminium(1+) |
| 10 | —(CH$_2$)$_{13}$CH$_3$ | —CH$_3$ | —(CH$_2$)$_4$— | 4-(methyl(tetradecyl)amino)-N,N,N-trimethylbutan-1-aminium(1+) |
| 11 | —(CH$_2$)$_{11}$CH$_3$ | —(CH$_2$)$_2$CH$_3$ | —(CH$_2$)$_4$— | 4-(dodecyl(propyl)amino-N,N,N-trimethylbutan-1-aminium(1+) |
| 12 | —(CH$_2$)$_{11}$CH$_3$ | —CH$_2$CH(CH$_3$)$_2$ | —(CH$_2$)$_4$— | 4-(dodecyl(isobutyl)amino)-N,N,N-trimethylbutan-1-aminium(1+) |
| 13 | —(CH$_2$)$_{11}$CH$_3$ | —(CH$_2$)$_2$CH$_3$ | —(CH$_2$)$_5$— | 5-(dodecyl(propyl)amino)-N,N,N-trimethylpentan-1-aminium(1+) |
| 14 | —(CH$_2$)$_{11}$CH$_3$ | —CH$_2$CH(CH$_3$)$_2$ | —(CH$_2$)$_5$— | 5-(dodecyl(isobutyl)amino)-N,N,N-trimethylpentan-1-aminium(1+) |
| 15 | —(CH$_2$)$_7$CH$_3$ | —CH$_3$ | —(CH$_2$)$_6$— | 6-(methyl(octyl)amino)-N,N,N-trimethylhexan-1-aminium(1+) |
| 16 | —(CH$_2$)$_9$CH$_3$ | —CH$_3$ | —(CH$_2$)$_6$— | 6-(decyl(methyl)amino)-N,N,N-trimethylhexan-1-aminium(1+) |
| 17 | —(CH$_2$)$_{11}$CH$_3$ | —CH$_3$ | —(CH$_2$)$_6$— | 6-(dodecyl(methyl)amino)-N,N,N-trimethylhexan-1-aminium(1+) |
| 18 | —(CH$_2$)$_{13}$CH$_3$ | —CH$_3$ | —(CH$_2$)$_6$— | 6-(methyl(tetradecyl)amino)-N,N,N-trimethylhexan-1-aminium(1+) |
| 19 | —(CH$_2$)$_7$CH$_3$ | —H | —(CH$_2$)$_3$— | 3-(octylamino)-N,N,N-trimethylpropan-1-aminium(1+) |
| 20 | —(CH$_2$)$_9$CH$_3$ | —H | —(CH$_2$)$_3$— | 3-(decylamino)-N,N,N-trimethylpropan-1-aminium(1+) |
| 21 | —(CH$_2$)$_{11}$CH$_3$ | —H | —(CH$_2$)$_3$— | 3-(dodecylamino)-N,N,N-trimethylpropan-1-aminium(1+) |
| 22 | —(CH$_2$)$_{13}$CH$_3$ | —H | —(CH$_2$)$_3$— | 3-(tetradecylamino)-N,N,N-trimethylpropan-1-aminium(1+) |

In the compounds having formula (I), including but not limited to those listed above in TABLE 1, counteranion X may be any counteranion typically present in an aqueous washing solution in which the cleaning composition may be used. In illustrative embodiments of such counteranions, X may be selected from the group consisting of chloride, bromide, iodide, hydroxide, nitrate, sulfate, and sulfite.

The compounds of formula (I) each comprise a tertiary amine group consisting of a nitrogen atom connected to each of groups $R^1$, $R^2$, and $R^3$. The tertiary amine group has a $pK_a$ that determines when the tertiary amine group is most likely to be protonated or deprotonated when the pH-switchable co-surfactant is present in an aqueous solution such as a wash liquor, for example. By definition, $pK_a$ of the pH-switchable co-surfactant is derived from a pH value of an aqueous solution containing the $pK_a$ of the pH-switchable co-surfactant, at which pH value exactly 50% of the molecules of the pH-switchable co-surfactant are protonated and exactly 50% of the molecules of the pH-switchable co-surfactant are deprotonated. It follows that the tertiary amine is more likely to be protonated when the aqueous solution has a pH less than the $pK_a$ of the pH-switchable co-surfactant and is more likely to be deprotonated when the aqueous solution has a pH greater than the $pK_a$ of the pH-switchable co-surfactant. Typically, washing solutions may have a washing pH of greater than 9.0 or greater than 10.0, whereas rinse water may have a pH of less than 9.0 for a first rinse, which gradually approaches a normal 6.5 or 7.0 of the water supplied for rinsing such as from a tap or basin, for example.

The inventors have found that the pH-switchable co-surfactant described herein function as good surfactants in aqueous solutions above the $pK_a$ of the pH-switchable co-surfactant. Under such circumstances, the pH-switchable co-surfactants may be capable of suds boosting benefits. On the other hand, the pH-switchable co-surfactants described herein tend to be rather poor surfactants in aqueous solutions with pH above the $pK_a$ of the pH-switchable co-surfactant.

Under such circumstances, the pH-switchable co-surfactants may collapse the suds in the aqueous solutions. Remarkably, the inventors have found that, if the pH-switchable co-surfactant is chosen such that its $pK_a$ is between the typical pH of the aqueous washing environment and the typical pH of rinse water, dual benefits may be realized. That is, a pH-switchable co-surfactant chosen with regard to its $pK_a$ may boost suds in wash water and may reduce or eliminate suds in rinse water.

Without intent to be bound by theory, it is believed that the $pK_a$ of the pH-switchable co-surfactants described herein are not the same in every formulation of the cleaning composition but, rather, depend at least in part on the structure and composition of the primary sudsing agent. For example, a given pH-switchable co-surfactant may have one $pK_a$ when it is the only sudsing ingredient (e.g., surfactant) in a cleaning composition but may have a different $pK_a$ when additional sudsing ingredients are present. The inventors have found that 3-(dodecyl(methyl)amino)-N,N,N-trimethylpropan-1-aminium bromide, the bromide salt of compound (3) in TABLE 1, may have a $pK_a$ of about 8.28 in water but may have higher $pK_a$ values in a solution further comprising an additional sudsing agent such as an anionic surfactant or a free fatty acid.

For example, the 3-(dodecyl(methyl)amino)-N,N,N-trimethylpropan-1-aminium bromide may have a $pK_a$ value of about 8.5 in combination with lauric acid (a fatty acid), of about 8.83 in combination with $AE_3S$ (defined above), of about 9.34 in combination with $AE_1S$ (defined above), of about 9.55 in combination with AS (defined above), or of about 9.60 in combination with LAS (defined above). Thus, in preferred embodiments the pH-switchable co-surfactant and the primary sudsing agent of the cleaning compositions may be chosen such that, in the particular cleaning composition, the pH-switchable co-surfactant has a $pK_a$ between the typical pH of a washing solution and the typical pH of rinsing water. In general, these preferred embodiments entail tailoring the selection pH-switchable co-surfactant and the primary sudsing agent such that the pH-switchable co-surfactant has a $pK_a$ of from about 8.0 to about 10.0, such as from about 8.5 to about 9.6. It may be especially preferred if the pH-switchable co-surfactant and the primary sudsing agent are chosen such that the $pK_a$ of the pH-switchable co-surfactant in the cleaning composition is approximately one-half the sum of the washing pH of the aqueous washing solution and the rinsing pH of the rinse water. Thereby, both a suds boosting benefit at washing pH and a suds reduction benefit at rinsing pH may be highly pronounced and maximized. In some illustrative embodiments, the combination of the pH-switchable co-surfactant and the primary sudsing agent may result in a rinse suds-suppression benefit, as whereby a ratio of rinse-suds volume at the rinsing pH to wash-suds volume, at the washing pH is less than or equal to 1:15, as determined according to testing methods described below in detail. In further embodiments, the combination of the pH-switchable co-surfactant and the primary sudsing agent result in a rinse suds-suppression benefit, whereby for a single concentration of cleaning composition in the aqueous wash solution, a ratio of suds volume at the rinsing pH in the aqueous wash solution to suds volume at the washing pH in the aqueous wash solution is less than or equal to 2:3.

Thus, it should be apparent that a unique synergy is present in the cleaning compositions described herein. The synergy is a result of aqueous solution interactions accomplished through the choices of the pH-switchable co-surfactant and the primary sudsing agent in consideration of the typical pH values of washing solutions and rinse waters.

Cleansing System

In addition to the pH-switchable sudsing system described above, the cleaning compositions according to embodiments herein further comprise a cleansing system that, when combined with the pH-switchable sudsing system, result in a cleaning composition suitable for use as a laundry detergent, a hand-dishwashing detergent, or a bar soap, for example.

In some embodiments, the cleaning composition is a laundry detergent which may include powder laundry detergent compositions, liquid laundry detergent compositions or laundry bar compositions. In such embodiments, the cleansing system may comprise one or more laundry detergent adjunct ingredients such as builders, polymers, brighteners, bluing agents, chelants, enzymes, perfumes, and water, for example. In other embodiments, the cleaning composition is a hand-dishwashing detergent. In such embodiments, the cleansing system may comprise one or more hand-dishwashing detergent adjuncts such as polymers, chelants, enzymes, perfumes, and water, for example. In still other embodiments, the cleaning composition is a personal bar soap. In such embodiments, the cleansing system may comprise one or more conditioning ingredients such as polymers, perfumes, fillers, humectants, sanitizing agents, antimicrobial agents, dyes, moisturizers, colorants, mildness aids, preservatives, clays, and water, for example. Regardless of whether the cleaning composition is formulated as a laundry detergent, a hand-dishwashing detergent, or a personal bar soap, in some embodiments the cleansing system may comprise a pH-control system. The pH control system is especially preferred when the cleaning composition is normally formulated to produce a washing pH of less than 10.0 in an aqueous washing solution at typical dilutions. In particular, because hand-dishwashing detergents typically produce a wash solution of about pH 9, the pH control system is especially preferred when the cleaning composition is a hand-dishwashing detergent. The above-listed ingredients are described in greater detail below.

pH Control System

The pH control system herein forms a buffering system which keeps the pH alkaline when the cleaning composition is being used in an aqueous washing solution to wash clothes, dishes, or body parts, for example. Without intent to be bound by theory, it is believed that an alkaline pH of the aqueous washing solution, particularly a pH of at least 10.0, may significantly improves cleaning performance of the cleaning composition against a variety of common soils such as greasy soils and body soils and also may result in boosting of suds formation in the aqueous cleaning solution. In preferred embodiments, the pH control system may be incorporated into the cleaning compositions to maintain the pH of the aqueous laundry solution above the $pK_a$ of the pH-switchable co-surfactant described above during washing. Optionally, the pH control system herein may contain both acids and bases to form a pH buffer system. In illustrative embodiments, the pH control system may comprise, for example, the sodium and/or potassium salts of carbonate, bicarbonate, citrate, silicate, hydroxide, and a combination thereof, or sodium carbonate, sodium silicate, sodium bicarbonate, and sodium hydroxide.

When a pH control system is present in the cleaning compositions to raise the pH of an aqueous washing solution, for example, in the rinse cycle, however, the pH control system breaks down due to excessive dilution. Thereby, the pH of the rinse bath may return to the natural pH of the rinse water, or close thereto, during successive rinses, as each rinse dilutes the pH control system further and further. Typically, the natural pH of the rinse water will be below 9.0 such as from 6.5 to 9.0, from 6.5 to 8.5, from 6.5 to 8.0, from 6.9 to 9.0, from 7.0 to 9.0, or from 7.0 to 8.0, for example. Even so, the first rinse bath after the article (e.g., fabric, dishes, skin) being cleaned is removed from the aqueous washing solution will often have a higher pH than successive rinse baths due to carry-over alkalinity from the aqueous washing solution. However, the pH decreases with each successive rinse bath so that the pH of the final rinse bath approaches the natural pH of the water used, which should be around 7.

Without intent to be bound by theory, it is believed that the lower the pH of the rinse water, the higher the charge density and, therefore, the greater reduction in suds during rinsing. In particular, it is believed that the lower pH may cause the tertiary amine of the pH-switchable co-surfactant molecules become protonated as the pH of the rinse water falls below the $pK_a$ of the pH-switchable co-surfactant. It is also believed that the protonated forms pH-switchable co-surfactant s according to formula (I) above are poor surfactants, whereas the deprotonated forms are good or very good surfactants. Thus, it is believed that the combination of an alkaline pH, the primary sudsing agents described herein, and the pH-switchable co-surfactants described herein may provide an unexpected synergy. In the rinse bath, the pH is typically less than about 9, or from about 6.5 to about 9, or from about 6.9 to about 8.6.

In embodiments, wherein the cleaning compositions are formulated as personal bar soaps, the pH of the bar soap may be greater than or equal to 10.7, preferably greater than or equal to 11, 11.5, 12, 12.5, 13, 13.5, or up to 14, as measured at around 25° C. using any commercially available pH meter. When a soap is tested in a solid form, it is first dissolved in distilled water to form an aqueous solution of a concentration of 10%. The pH of this aqueous solution is then tested to be representative of the bar soap.

Cleaning compositions formulated as bar soaps, therefore, may comprise a pH-adjusting agent in a sufficient amount to attain the above mentioned pH. The pH adjusting agents useful for the present cleaning compositions include alkalizing agents. Suitable alkalizing agents include, for example, ammonia solution, triethanolamine, diethanolamine, monoethanolamine, potassium hydroxide, sodium hydroxide, sodium phosphate dibasic, soluble carbonate salts, ammonia solution, triethanolamine, diethanolamine, monoethanolamine, potassium hydroxide, sodium hydroxide, sodium phosphate dibasic, soluble carbonate salts, and combinations thereof.

The amount of the pH adjusting agent for use in the present pH-control system and required to attain the requisite pH can be calculated by one skilled in the art following known chemical parameters, for example, the $pK_a$ value of the pH-adjusting agent.

In one illustrative embodiment, the cleaning composition may be a bar soap and may comprise, in addition to the pH-switchable sudsing system, a soluble carbonate salt in an amount effective to attain a pH of greater than or equal to 10.7 to decrease discoloration. Soluble carbonate salts may include those carbonates and bicarbonates that have a solubility of greater than or equal to 0.01 g/mL in water at 20° C. Such carbonates may be selected from a group consisting of sodium carbonate, potassium carbonate, ammonium carbonate, aluminum carbonate, magnesium carbonate, sodium bicarbonate, potassium bicarbonate, ammonium bicarbonate and combinations thereof. Thus, the cleaning compositions may comprise a soluble carbonate salt in an amount effective to prevent discoloration. For example, soluble carbonate salt may be present in the cleaning composition in an amount ranging from about 0.3%, 0.5%, 0.8%, 1% or 1.5% to about 2%, 2.5%, 5%, 10% or 20% by weight, based on the total weight of the cleaning composition.

Additional Ingredients of the Cleansing System

As noted above, the cleaning compositions may comprise additional adjunct components. The precise nature of these additional adjunct components, and levels of incorporation thereof, will depend on the physical form of the composition and the nature of the operation for which it is to be used. Suitable adjunct materials include, but are not limited to, flocculating aids, chelating agents, dye transfer inhibitors, enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, and/or pigments. In addition to the disclosure below, suitable examples of such other adjuncts and levels of use are found in U.S. Pat. Nos. 5,576,282, 6,306,812 B1 and 6,326,348 B1 that are incorporated by reference. Such one or more adjuncts may be present as detailed below:

BUILDERS—The cleansing system of the cleaning compositions may contain a builder, or an inorganic builder. The inorganic builder is typically selected from the group consisting of a phosphate builder, a silicate builder, a zeolite builder, and a mixture thereof. The phosphate builder herein includes the alkali metal, ammonium and alkanolammonium salts of polyphosphate, orthophosphate and/or metaphosphate; or the alkali metal salts of polyphosphate, orthophosphate and/or metaphosphate; or the sodium and potassium salts of polyphosphate, orthophosphate and/or metaphosphate; such as, for example, sodium tripolyphosphate (STPP).

The inorganic builder may include an alkali metal silicate, a zeolite, and a mixture thereof. Both sheet silicates and amorphous silicates are useful herein as are zeolite A, zeolite X, zeolite P, zeolite MAP, and a mixture thereof. The detergent composition herein typically contains from about 1% to about 40%, or from about 3% to about 35%, or from about 5% to about 30% builder.

The balance of the laundry detergent typically contains from about 5% to about 70%, or about 10% to about 60% adjunct ingredients such as a bleach, a polymer, a bluing agent, a brightener, a chelant, an enzyme, a perfume, a non-anionic surfactant, a suds suppressor, etc. which are well known in the art.

BLUING AGENTS—A bluing agent is typically a slightly bluish dye and/or pigment which attaches to fabrics and which thereby helps to hide yellowish tinges and colors on fabrics so as to make the fabric appear whiter. Bluing agents suitable for use herein include: Polar Brilliant Blue GAW 180 percent sold by Ciba-Geigy S. A., Basel, Switzerland (similar to C.I. ["Color Index"] 61135—Acid Blue 127); FD&C Blue No. 1 (C.I. 42090), Rhodamine BM (C.I. 45170); Pontacyl Light Yellow 36 (similar to C.I. 18820); Acid yellow 23; Pigmasol blue; Acid blue 3; Polar Brilliant Blue RAW (C.I. 61585—Acid Blue 80); Phthalocyanine Blue (C.I. 74160); Phthalocyanine Green (C.I. 74260); and Ultramarine Blue (C.I. 77007—Pigment Blue 29). Additional examples of suitable bluing agents are described in U.S. Pat. No. 3,931,037 issued Jan. 6, 1976 to Hall and U.S. Pat. No. 5,605,883 issued Feb. 25, 1997 to Iliff, et al. In an embodiment herein the bluing agent is ultramarine blue which is available form a variety of suppliers, worldwide.

BRIGHTENERS—Brighteners convert non-visible light into visible light thereby making fabric and clothes appear brighter, whiter and/or their colors more vibrant. Non-limiting examples of brighteners useful herein include brightener 15, brightener 49, brightener, manufactured by Ciba Geigy, Paramount, Shanghai Yulong and others. Bluing agents and brighteners are typically present at levels of from about 0.005% to about 3%.

CHELANTS—The chelant useful herein may be selected from all compounds in any suitable amount or form that bind with metal ions to control the adverse effects of heavy metal contamination or water hardness (for example, calcium and magnesium ions) in an aqueous bath. Any multidentate ligand is suitable as a chelating agent. For example, suitable chelating agents can include, but are not limited to a carboxylate, a phosphate, a phosphonate, a polyfunctionally-substituted aromatic compound, a polyamine, the alkali metal, ammonium or substituted ammonium salts or complexes of these chelating agents, and a mixture thereof.

PERFUME—The perfume herein provides aesthetic impact to the fabric either during or after laundering. Perfumes are available from, e.g., Givaudan, International Flavors & Fragrances, etc., and are typically present at from about 0.001% to about 5%, or from about 0.01% to about 3%, or from about 0.1% to about 2.5%.

FLOCCULATING AID—The cleansing system may further comprise a flocculating aid. Typically, the composition comprises at least 0.3% by weight of the composition of a flocculating aid. The composition may also be substantially free of flocculating aid. Typically, the flocculating aid is polymeric. Typically the flocculating aid is a polymer comprising monomer units selected from the group consisting of ethylene oxide, acrylamide, acrylic acid and mixtures thereof. Typically the flocculating aid is a polyethyleneoxide. Typically the flocculating aid has a molecular weight of at least 100,000 Da, in particular from 150,000 Da to 5,000,000 Da or even from 200,000 Da to 700,000 Da.

BLEACHING AGENT—The cleansing system may comprise one or more bleaching agents. In general, when a bleaching agent is used, the compositions of the present invention may comprise from about 0.1% to about 50% or even from about 0.1% to about 25% bleaching agent by weight of the subject detergent composition. When present, suitable bleaching agents include bleaching catalysts, photobleaches for example Vitamin K3 and zinc or aluminium phtalocyanine sulfonate; bleach activators such as tetraacetyl ethylene diamine (TAED) and nonanoyloxybenzene sulphonate (NOBS); hydrogen peroxide; pre-formed peracids; sources of hydrogen peroxide such as inorganic perhydrate salts, including alkali metal salts such as sodium salts of perborate (usually mono- or tetra-hydrate), percarbonate, persulphate, perphosphate, persilicate salts and mixtures thereof, optionally coated, suitable coatings including inorganic salts such as alkali metal; and mixtures thereof. The amounts of hydrogen peroxide source and peracid or bleach activator may be selected such that the molar ratio of available oxygen (from the peroxide source) to peracid is from 1:1 to 35:1, or even 2:1 to 10:1

FLUORESCENT WHITENING AGENT—The cleansing system may contain components that may tint articles being cleaned, such as fluorescent whitening agent. When present, any fluorescent whitening agent suitable for use in a detergent composition may be used in the cleaning compositions described herein. The most commonly used fluorescent whitening agents are those belonging to the classes of diaminostilbene-sulphonic acid derivatives, diarylpyrazoline derivatives and bisphenyl-distyryl derivatives. Typical fluorescent whitening agents are Parawhite KX, supplied by Paramount Minerals and Chemicals, Mumbai, India; Tinopal® DMS and Tinopal® CBS available from Ciba-Geigy AG, Basel, Switzerland. Tinopal® DMS is the disodium salt of 4,4'-bis-(2-morpholino-4 anilino-s-triazin-6-ylamino)stilbene disulphonate. Tinopal® CBS is the disodium salt of 2,2'-bis-(phenyl-styryl)disulphonate.

FABRIC HUEING AGENTS—Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof.

POLYMERIC DISPERSING AGENTS—The cleansing system can contain additional polymeric dispersing agents. These polymeric dispersing agents, if included, are typically at levels up to about 5%, typically from about 0.2% to about 2.5%, more typically from about 0.5% to about 1.5%. Suitable polymeric dispersing agents, include polymeric polycarboxylates, substituted (including quarternized and oxidized) polyamine polymers, and polyethylene glycols, such as: acrylic acid-based polymers having an average molecular of about 2,000 to about 10,000; acrylic/maleic-based copolymers having an average molecular weight of about 2,000 to about 100,000 and a ratio of acrylate to maleate segments of from about 30:1 to about 1:1; maleic/acrylic/vinyl alcohol terpolymers; polyethylene glycol (PEG) having a molecular weight of about 500 to about 100,000, typically from about 1,000 to about 50,000, more typically from about 1,500 to about 10,000; and water soluble or dispersible alkoxylated polyalkyleneamine materials.

POLYMERIC SOIL RELEASE AGENT—The cleansing system can also contain polymeric soil release agent. polymeric soil release agent, or "SRA," have hydrophilic segments to hydrophilize the surface of hydrophobic fibers such as polyester and nylon, and hydrophobic segments to deposit upon hydrophobic fibers and remain adhered thereto through completion of washing and rinsing cycles, thereby serving as an anchor for the hydrophilic segments. This can enable stains occurring subsequent to treatment with the SRA to be more easily cleaned in later washing procedures. Preferred SRAs include oligomeric terephthalate esters; sulfonated product of a substantially linear ester oligomer comprised of an oligomeric ester backbone of terephthaloyl and oxyalkyleneoxy repeat units and allyl-derived sulfonated terminal moieties covalently attached to the backbone; nonionic end-capped 1,2-propylene/polyoxyethylene terephthalate polyesters; an oligomer having empirical formula $(CAP)_2$ $(EG/PG)_5$ $(T)_5$ $(SIP)_1$ which comprises terephthaloyl (T), sulfoisophthaloyl (SIP), oxyethyleneoxy and oxy-1,2-propylene (EG/PG) units and which is typically terminated with end-caps (CAP), typically modified isethionates, as in an oligomer comprising one sulfoisophthaloyl unit, 5 terephthaloyl units, oxyethyleneoxy and oxy-1,2-propyleneoxy units in a defined ratio, typically about 0.5:1 to about 10:1, and two-end-cap units derived from sodium 2-(2-hydroxyethoxy)-ethanesulfonate; oligomeric esters comprising: (1) a backbone comprising (a) at least one unit selected from the group consisting of dihydroxy sulfonates, polyhydroxy sulfonates, a unit which is at least trifunctional whereby ester linkages are formed resulting in a branched oligomer backbone, and combinations thereof; (b) at least one unit which is a terephthaloyl moiety; and (c) at least one unsulfonated unit which is a 1,2-oxyalkyleneoxy moiety; and (2) one or more capping units selected from nonionic capping units, anionic capping units such as alkoxylated, typically ethoxylated, isethionates, alkoxylated propanesulfonates, alkoxylated propanedisulfonates, alkoxylated phenolsulfonates, sulfoaroyl derivatives and mixtures thereof. Preferred esters have an empirical formula $((CAP)_a(EG/PG)_b(DEG)_c\ PEG)_d(T)_e(SIP)_f(SEG)_g(B)_h)$, where CAP, EG/PG, PEG, T and SIP are as defined hereinabove, DEG represents di(oxyethylene)oxy units, SEG represents units derived from the sulfoethyl ether of glycerin and related moiety units, B represents branching units which are at least trifunctional whereby ester linkages are formed resulting in a branched oligomer backbone, a is from about 1 to about 12, b is from about 0.5 to about 25, c is from 0 to about 12, d is from 0 to about 10, b+c+d totals from about 0.5 to about 25, e is from about 1.5 to about 25, f is from 0 to about 12; e+f totals from about 1.5 to about 25, g is from about 0.05 to about 12; h is from about 0.01 to about 10, and a, b, c, d, e, f, g, and h represent the average number of moles of the corresponding units per mole of the ester; and the ester has a molecular weight ranging from about 500 to about 5,000; and; cellulosic derivatives such as the hydroxyether cellulosic polymers available as METHOCEL® from Dow; the $C_1$-$C_4$ alkyl celluloses and $C_4$ hydroxyalkyl celluloses, see U.S. Pat. No. 4,000,093, issued Dec. 28, 1976 to Nicol et al., and the methyl cellulose ethers having an average degree of substitution (methyl) per anhydroglucose unit from about 1.6 to about 2.3 and a solution viscosity of from about 80 to about 120 centipoise measured at 20° C. as a 2% aqueous solution. Such materials are available as METOLOSE SM100® and METOLOSE SM200®, which are the trade names of methyl cellulose ethers manufactured by Shinetsu Kagaku Kogyo KK.

ENZYMES—The cleansing system may further comprise an enzyme. When present in the cleansing system, the enzymes may be present at levels from about 0.00001% to about 2%, from about 0.0001% to about 1% or even from about 0.001% to about 0.5% or 0.02% enzyme protein by weight of the cleaning composition. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof.

ENZYME STABILIZERS—Enzymes for use the cleansing system can be stabilized by various techniques. The enzymes employed herein can be stabilized by the presence of water-soluble sources of calcium and/or magnesium ions in the finished compositions that provide such ions to the enzymes. In case of aqueous compositions comprising protease, a reversible protease inhibitor, such as a boron compound, can be added to further improve stability.

CATALYTIC METAL COMPLEXES—The cleansing system may comprise catalytic metal complexes. When present, one type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the cleaning compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; U.S. Pat. No. 5,595,967. Such cobalt catalysts are readily prepared by known procedures, such as taught for example in U.S. Pat. No. 5,597,936, and U.S. Pat. No. 5,595,967.

Cleaning compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

SOFTENING SYSTEM—the cleansing system may comprise a softening agent such as clay for softening through the wash. The composition may additionally comprise a charged polymeric fabric-softening boosting component.

COLORANT—the cleansing system may comprise a colorant, typically a dye or a pigment. Particularly, preferred dyes are those which are destroyed by oxidation during a laundry wash cycle. To ensure that the dye does not decompose during storage it is preferable for the dye to be stable at temperatures up to 40° C. The stability of the dye in the composition can be increased by ensuring that the water content of the composition is as low as possible. If possible, the dyes or pigments should not bind to or react with textile fibers. If the colorant does react with textile fibers, the color imparted to the textiles should be destroyed by reaction with the oxidants present in laundry wash liquor. This is to avoid coloration of the textiles, especially over several washes. Particularly, preferred dyes include but are not limited to Basacid® Green 970 from BASF and Monastral blue from Albion.

HUMECTANTS—In embodiments, wherein the cleaning composition is formulated as a personal bar soap, the cleansing system may comprise one or more humectants. The humectants that can be included in the cleansing system are generally selected from the group consisting of polyhydric alcohols, water soluble alkoxylated nonionic polymers, and mixtures thereof and are preferably used at amounts by weight of the composition of from about 0.1% to about 20%, more preferably from about 0.5% to about 15%, and more preferably from about 1% to about 10%.

Humectants such as glycerin can be included in the cleansing system as a result from the production of the soap. For example, glycerin can be a by-product after saponification of the cleaning composition. The glycerin or at least a portion thereof can be left in the cleaning composition. The amount of humectant in the cleaning composition is typically no more than about 1%, by weight of the cleaning composition.

In one embodiment, it can be advantageous to purposely add additional humectant such as glycerin to the composition. The additional humectant can be added to a soap noodle used in preparation of the present compositions. The additional humectant can be added either before the drying process of the neat soap containing about 30% water, or after the drying process (e.g. into an amalgamator). The total level of humectant in this case will typically be at least about 1%, preferably at least about 2%, more preferably at least about 3%, by weight of the composition. Incorporating additional humectant into the antimicrobial bar composition herein can result in a number of benefits such as improvement in hardness of the cleaning composition, decreased Water Activity of the cleaning composition, and lowering the weight loss rate of the cleaning composition over time due to water evaporation.

Humectants useful herein include glycerin, sorbitol, propylene glycol, butylene glycol, hexylene glycol, ethoxylated glucose, 1,2-hexane diol, hexanetriol, dipropylene glycol, erythritol, starch, trehalose, diglycerin, xylitol, maltitol, maltose, glucose, fructose, sodium chondroitin sulfate, sodium hyaluronate, sodium adenosin phosphate, sodium lactate, pyrrolidone carbonate, glucosamine, cyclodextrin, salts such as chlorides, sulfates, carbonates, and mixtures thereof. Water soluble alkoxylated nonionic polymers useful for the antimicrobial bar composition herein include polyethylene glycols and polypropylene glycols having a molecular weight of up to about 1000 such as those with CTFA names PEG-200, PEG-400, PEG-600, PEG-1000, and mixtures thereof.

INORGANIC SALTS—In embodiments, wherein the cleaning composition is formulated as a personal bar soap, the cleansing system may include inorganic salts. The inorganic can help maintain a particular water content or level (e.g. a Water Activity) of a personal bar soap and improve hardness of the bar soap. The inorganic salts also help bind the water in the antimicrobial bar composition thereby preventing water loss by evaporation or other means. The cleansing system can optionally include from about 0.01% to about 15%, preferably from about 1% to about 12%, and more preferably from about 2.5% to about 10.5%, by weight of the cleaning composition, of inorganic salt. Higher levels of inorganic salts are generally preferred. Suitable inorganic salts that can be included in the antimicrobial bar composition include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and the like. I n preferred embodiments, the inorganic salts that can be included in the cleansing system include sodium tripolyphosphate, magnesium salts (such as magnesium sulfate), and/or tetrasodium pyrophosphate. Magnesium salts, when used as an ingredient in the cleaning compositions comprising soap, tend to be converted to magnesium soap in the finished product. Sodium tripolyphosphate, magnesium salts (and as a result magnesium soap), and/or tetrasodium pyrophosphate are preferred in the cleansing system. Sodium tripolyphosphate is also preferred as it can tend to promote the generation of lather as the cleaning composition is used by a consumer for cleansing skin.

ANTIBACTERIAL AGENTS—In embodiments, wherein the cleaning composition is formulated as a personal bar soap, the cleansing system may include one or more antibacterial agents that can serve to enhance the antimicrobial effectiveness of the cleaning compositions. When an antibacterial agent is present, the cleaning composition antimicrobial bar composition can include from about 0.001% to about 2%, preferably from about 0.01% to about 1.5%, more preferably from about 0.1% to about 1%, by weight of the cleaning composition. Examples of antibacterial agents that can be employed are the carbanilides, for example, triclocarban (also known as trichlorocarbanilide), triclosan, a halogenated diphenylether available as DP-300 from Ciba-Geigy, hexachlorophene, 3,4,5-tribromosalicylanilide, and salts of 2-pyridinethiol-1-oxide, salicylic acid and other organic acids. Other suitable antibacterial agents are described in detail in U.S. Pat. No. 6,488,943 (referred to as antimicrobial actives).

BRIGHTENERS—In embodiments, wherein the cleaning composition is formulated as a personal bar soap, the cleansing system may include brighteners at an amount of from about 0.001% to about 1%, preferably from about 0.005% to about 0.5%, and more preferably from about 0.01% to about 0.1%, by weight of the cleaning composition. Examples of suitable brighteners in the present cleaning compositions include disodium4,4'-bis-(2-sulfostyril)-biphenyl (commercially available under the tradename Brightener-49, from Ciba Specialty Chemicals); disodium-4,4'-bis-[(4,6-di-anilino-s-triazine-2-yl)-amino]-2,2'-stilbenedisulfonate (commercially available under the tradename Brightener 36, from Ciba Specialty Chemicals); 4,4'-bis-[(4-anilino-6-morpholino-s-triazine-2-yl)-amino]-2,2'-stilbenedisulfonate (commercially available under the tradename Brightener 15, from Ciba Specialty Chemicals); and 4,4'-bis-[(4-anilino-6-bis-2(2-hydroxyethyl)-amino-s-triazine-2-yl)-amino]-2,2'-stilbenedisulfonate (commercially available under the tradename Brightener 3, from Ciba Specialty Chemicals); and mixtures thereof.

SILICAS—In embodiments, wherein the cleaning composition is formulated as a personal bar soap, the cleansing system may include silica, or silicon dioxide at an amount of from about 0.1% to about 15%, preferably from about 1% to about 10%, and more preferably from about 3% to about 7%, by weight of the cleaning composition. Silica is available in a variety of different forms include crystalline, amorphous, fumed, precipitated, gel, and colloidal. Preferred forms herein are fumed and/or precipitated silica.

Thickening silica typically has smaller particle size versus normal abrasive silica and is preferred herein. The average particle size of thickening silica is preferably from about 9 µm to about 13 µm, as opposed to normal abrasive silica which has an average particle size of from about 20 µm to about 50 µm. Due to the surface of the preferred thickening silica having a relatively large amount of silinol groups, it can bind the water and build the right texture for the present bar compositions. The silinol groups tend to form hydrogen bonds wherein three-dimensional networks are fabricated to act like a spring in the soap phase to deliver good foaming and good texture. The thickening silica preferably has a high oil absorbency value (DBP), normally indicating porosity and large surface area, and is preferably greater than about 250 (g/100 g), and more preferably greater than about 300 (g/100 g).

Non-limiting examples of suitable thickening silica include: SIDENT 22S commercially available from Degussa; ZEODENT 165 commercially available from J. M. Huber Corp.; SORBOSIL TC15 commercially available from Ineos Silicas; TIXOSIL 43 commercially available from Rhodia; and SYLOX 15× commercially available from W. R. Grace Davidson.

STRUCTURANTS—In embodiments, wherein the cleaning composition is formulated as a personal bar soap, the cleansing system may include structurants such as raw starch (e.g. corn, rice, potato, wheat, and the like), pregelatinzed starch, carboxymethyl cellulose, polyacrylate polymer available under the trade name of Stabylene from BF Goodrich and Carbopol from 3V Corporation, carregeenan, xanthan gum, polyethylene glycol, polyethylene oxide, and the like. Preferred structurants include raw starch and/or pregelatinized starch.

MOISTURIZERS/EMOLLIENTS—In embodiments, wherein the cleaning composition is formulated as a personal bar soap, the cleansing system may include moisturizers to provide the skin conditioning benefits and to improve the mildness of the cleaning composition. The selection of the levels and types of moisturizers to be incorporated into the cleaning composition is made without adversely affecting the stability of the product or its in-use characteristics, thereby delivering good moisturization and lather. Both occlusive and nonocclusive moisturizers are suitable for use in the present invention. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and lanolin alcohol (e.g., Solulan-75).

When moisturizers are used in the cleaning systems, they are used at levels of from about 2% to about 20% by weight of the cleaning composition. The preferred and more preferred levels of moisturizers are, respectively, 4% to 15% and 8% to 12%. The preferred moisturizers are the coconut and tallow fatty acids. Some other preferred moisturizers are the nonocclusive liquid water-soluble polyols (e.g., glycerin) and the essential amino acid compounds found naturally in the skin.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic acid, lactic acid, oleic acid, stearic acid, isostearic acid, myristic acid or linoleic acid, as well as many of their corresponding alcohol esters (sodium isostearoyl-2-lactylate, sodium capryl lactylate), hydrolyzed protein and other collagen-derived proteins, aloe vera gel and acetamide MEA (acetmonoethanolamide).

Cleaning Composition Form and Process for Making:

When formed as a laundry detergent, the cleaning compositions may be made in the form of a water-soluble granule formed by agglomeration and/or spray drying. Such a granular laundry detergent is usually composed of particles having a weight-average particle size (diameter) of from about 50 µm to about 3 mm, or from about 100 µm to about 1 mm. In an embodiment herein the laundry detergent is in the form of a liquid or a gel, which may be either structured or an unstructured. Manufacturing processes for such laundry detergents may be either batch or continuous and are well-known in the art.

According to other embodiments, the cleaning compositions may be in any liquid or solid form, in the form of gel, paste, dispersion, preferably a colloidal dispersion or any combination thereof. The cleaning composition is preferably in a solid form or in the form of a paste. The cleaning composition may be in particulate form, for example in free-flowing particulate form. The composition in solid form can be in the form of an agglomerate, granule, flake, extrudate, bar, tablet or any combination thereof. The cleaning composition may be capable of cleaning and/or softening fabric during a laundering process or may be a dish care composition.

When the cleaning composition is for example in particulate form, it is typically in free-flowing particulate form, although the composition may be in any liquid or solid form. The composition in solid form can be in the form of an agglomerate, granule, flake, extrudate, bar, tablet or any combination thereof. The solid composition can be made by methods such as dry-mixing, agglomerating, compaction, spray drying, pan-granulation, spheronization or any combination thereof. The solid composition typically has a bulk density of from 300 g/L to 1,500 g/L, typically from 500 g/L to 1,000 g/L.

The cleaning compositions described herein can be used as a wide range of consumer cleaning products including powders, liquids, granules, gels, pastes, tablets, pouches, bars, types delivered in dual-compartment containers, spray or foam detergents and other homogeneous or multiphasic consumer cleaning product forms. They can be used or applied by hand and/or can be applied in unitary or freely alterable dosage, or by automatic dispensing means, or are useful in appliances such as washing-machines or dishwashers or can be used in institutional cleaning contexts, including for example, for personal cleansing in public facilities, for bottle washing, for surgical instrument cleaning or for cleaning electronic components.

One of the preferred methods of delivering surfactant in consumer products is to make surfactant agglomerate particles, which may take the form of flakes, prills, marumes, noodles, ribbons, but preferably take the form of granules. A preferred way to process the particles is by agglomerating powders (e.g. aluminosilicate, carbonate) with high active surfactant pastes and to control the particle size of the resultant agglomerates within specified limits. Such a process involves mixing an effective amount of powder with a high active surfactant paste in one or more agglomerators such as a pan agglomerator, a Z-blade mixer or more preferably an in-line mixer such as those manufactured by Schugi (Holland) BV, 29 Chroomstraat 8211 AS, Lelystad, Netherlands, and Gebruder Lödige Maschinenbau GmbH, D-4790 Paderbom 1, Elsenerstrasse 7-9, Postfach 2050, Germany. Most preferably a high shear mixer is used, such as a Lödige CB (Trade Name).

A high active surfactant paste comprising from 50% by weight to 95% by weight, preferably 70% by weight to 85% by weight of surfactant is typically used. The paste may be pumped into the agglomerator at a temperature high enough to maintain a pumpable viscosity, but low enough to avoid degradation of the anionic surfactants used. An operating temperature of the paste of 50° C. to 80° C. is typical.

The cleaning compositions can be used in bar soaps, including personal cleansing bars as well as so-called laundry bars (see, for example WO 96/35772 A); including both the syndet and soap-based types and types with softener (see U.S. Pat. No. 5,500,137 or WO 96/01889 A); such compositions can include those made by common soap-making techniques such as plodding and/or more unconventional techniques such as casting, absorption of surfactant into a porous support, or the like. Other bar soaps (see for example BR 9502668; WO 96/04361 A; WO 96/04360 A; U.S. Pat. No. 5,540,852) are also included. Other handwash detergents include those such as are described in GB 2,292,155 A and WO 96/01306 A.

Bar soaps can be made via a number of different processes known in the art. Preferably, the present compositions are made via a milling process, resulting in milled bar compositions. A typical milling process of manufacturing a bar composition includes: (a) a crutching step in which the soap is made, (b) a vacuum drying step in which the soap is made into soap noodles, (c) an amalgamating step in which the soap noodles are combined with other ingredients of the bar composition, (d) a milling step in which a relatively homogeneous mixture is obtained, (e) a plodding step in which the soap mixture is extruded as soap logs and then cut into soap plugs, and (f) a stamping step in which the soap plugs are stamped to yield the finished bar soap composition.

Additionally, soaps may be made by the classic kettle boiling process or modern continuous soap manufacturing processes, wherein natural fats and oils such as tallow or coconut oil or their equivalents are saponified with an alkali metal hydroxide using procedures well known to those skilled in the art. Alternatively, the soaps may be made by neutralizing fatty acids, such as lauric acid ($C_{12}$), myristic acid ($C_{14}$), palmitic acid ($C_{16}$), or stearic acid ($C_{18}$) with an alkali metal hydroxide or carbonate.

Methods for Use

In preferred embodiments, the cleaning compositions herein may be incorporated into laundry detergents intended for hand-washing of laundry, rather than machine-washing. In a method of hand washing a material such as a fabric, for example, using the cleaning compositions described herein, the hand-washing method may comprise (A) diluting a cleaning composition according to embodiments described herein in water at a weight ratio of water to the cleaning composition of from about 1:150 to about 1:1000 to form a laundry liquor having a pH, wherein the pH-switchable co-surfactant of the cleaning composition each have a $pK_a$; (B) hand washing a fabric in the laundry liquor; (C) maintaining pH of the laundry liquor above the $pK_a$ of the pH-switchable co-surfactant during the washing; and (D) rinsing the fabric in a rinse bath having a pH less than the $pK_a$ of the pH-switchable co-surfactant. When these method steps are performed, the pH-switchable co-surfactant may then form an ion pair with the primary sudsing agent during the rinsing. In preferred embodiments, the pH of the laundry liquor is from about 10 to about 13 and the pH of the rinse bath is less than 9 or less than 8. Likewise, it may be preferable that the $pK_a$ of the pH-switchable co-surfactant in the cleaning composition is about one-half the sum of the pH of the laundry liquor and the pH of the rinse bath. The method for hand-washing a fabric is generally applicable as a portion of a method of saving water, in combination with other apparent steps as part of a water-saving strategy in a location where water is scarce, for example.

The cleaning compositions herein are especially well-suited for use in a hand-washing context and in hard water conditions where the water hardness is between about 10 ppm to about 600 ppm; or from about 15 ppm to about 340 ppm; or from about 17 ppm to about 300 ppm, or from about 20 ppm to about 230 ppm of hard water ions such as $Ca^{2+}$, $Mg^{2+}$, etc., or such as $Ca^{2+}$ and/or $Mg^{2+}$. For hand-washing, the laundry detergent is typically diluted by a factor of from about 1:150 to about 1:1000, or about 1:200 to about 1:500 by weight, by placing the laundry detergent in a container along with wash water to form a laundry liquor. The container is typically square, rectangular, oval or round and is wider than it is deep. The wash water used to form the laundry liquor is typically whatever water is easily available, such as tap water, river water, well water, etc. The temperature of the wash water may range from about 2° C. to about 50° C., or from about 5° C. to about 40° C., or from 10° C. to 40° C., although higher temperatures may be used for soaking and/or pretreating.

The laundry detergent and wash water are usually agitated to evenly disperse and/or either partially or completely dissolve the detergent and thereby form a laundry liquor. Such agitation forms suds, typically voluminous and creamy suds. The dirty laundry is added to the laundry liquor and optionally soaked for a period of time. Such soaking in the laundry liquor may be overnight, or for from about 1 minute to about 12 hours, or from about 5 minutes to about 6 hours, or from about 10 minutes to about 2 hours. In a variation herein, the laundry is added to the container either before or after the wash water, and then the laundry detergent is added to the container, either before or after the wash water.

The method herein optionally includes a pre-treating step where the user pre-treats the laundry with the laundry detergent to form pre-treated laundry. In such a pre-treating step, the laundry detergent may be added directly to the laundry to form the pre-treated laundry, which may then be optionally scrubbed, for example, with a brush, rubbed against a surface, or against itself before being added to the wash water and/or the laundry liquor. Where the pre-treated laundry is added to water, then the diluting step may occur as the laundry detergent from the pre-treated laundry mixes with the wash water to form the laundry liquor.

The laundry is then hand-washed by the user who typically kneels next to, sits next to or leans over the container. Once the laundry is hand-washed, then the laundry may be wrung out and put aside while the laundry liquor is either used for additional laundry, poured out, etc. The same container may be used for both hand-washing the laundry and rinsing the laundry. Thus, the laundry liquor may often be emptied from the container, so that rinse water (often from the same source as the wash water) may be added; or a separate rinse container or area may be used. In cases where a rinse container is used, the laundry and rinse water are added either one after another or concurrently to form a rinse bath, and then it is common practice to agitate the laundry to remove the surfactant residue. Without intending to be limited by theory, it is believed that the pH-switchable co-surfactant may also reduce the formation of new suds during such agitation.

The laundry may be soaked in the rinse water and then the laundry may be wrung out, and put aside. The used rinse water is typically discarded and new rinse water is prepared. This rinsing step is repeated until the user subjectively judges that the laundry is clean—which typically means "until no more suds are present on the rinse water." It has been found that with a typical hand-washing liquid laundry detergent, the user will rinse a total of from about 3 to about 6 times. However, it has been found that suds on the rinse water is not necessarily an accurate measurement of when the surfactant is actually removed from the laundry, because visible suds may be caused by the residual laundry liquor in the container, suds physically sticking to the fabric, etc.

With the laundry detergent herein, the pH-switchable co-surfactant can reduce the perceived need for so many rinses by reducing the suds present during the rinse cycle. Thus, the actual number of rinses with the liquid laundry detergent herein should be reduced, and thus may more correctly correspond with the actual number needed to remove an acceptable level of surfactant residue. This in turn decreases the rinsing needed and saves significant water, effort and resources. In fact, it has been surprisingly found that the average number of rinses using the invention may be half, or one third of the number of rinses using a comparable product lacking the silicone-containing suds suppression system. The number of rinses when using the liquid laundry detergent herein is typically from about 1 to about 3, or from about 1 to about 2. In an embodiment herein, the user may add to one or more rinses a fabric conditioner, a fabric softener, a laundry sour, etc. as desired.

When the cleaning compositions herein are formulated as laundry detergents intended for machine-washing applications, typical machine laundry methods also may be used. Machine laundry methods herein generally comprise treating soiled laundry with an aqueous wash solution in a washing machine having dissolved or dispensed therein an effective amount of a machine laundry detergent composition in accord with the invention. By an effective amount of the detergent composition it is here meant from 40 g to 300 g of product dissolved or dispersed in a wash solution of volume from 5 to 65 liters, as are typical product dosages and wash solution volumes commonly employed in conventional machine laundry methods.

As noted, surfactants are used herein in combination with the pH-switchable co-surfactants, at levels which are effective for achieving at least a directional improvement in cleaning performance. In the context of a fabric laundry composition, such "usage levels" can vary widely, depending not only on the type and severity of the soils and stains, but also on the wash water temperature, the volume of wash water and the type of washing machine.

In a preferred use aspect a dispensing device may be employed in the washing method. The dispensing device may charged with the cleaning composition, and may be used to introduce the cleaning composition directly into the drum of a washing machine before the commencement of the wash cycle. Its volume capacity should be such as to be able to contain sufficient detergent product as would normally be used in the washing method.

Once the washing machine has been loaded with laundry the dispensing device containing the detergent product is placed inside the drum. At the commencement of the wash cycle of the washing machine water is introduced into the drum and the drum periodically rotates. The design of the dispensing device should be such that it permits containment of the dry detergent product but then allows release of this product during the wash cycle in response to its agitation as the drum rotates and also as a result of its contact with the wash water.

Alternatively, the dispensing device may be a flexible container, such as a bag or pouch. The bag may be of fibrous construction coated with a water impermeable protective material so as to retain the contents, such as is disclosed in European published Patent Application No. 0018678. Alternatively it may be formed of a water-insoluble synthetic polymeric material provided with an edge seal or closure designed to rupture in aqueous media as disclosed in European published Patent Application Nos. 0011500, 0011501, 0011502, and 0011968. A convenient form of water frangible closure comprises a water soluble adhesive disposed along and sealing one edge of a pouch formed of a water impermeable polymeric film such as polyethylene or polypropylene.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. One of ordinary skill in the art will understand that any numerical values inherently contain certain errors attributable to the measurement techniques used to ascertain the values.

EXAMPLES

The following examples are offered by way of illustration only and are not intended to limit the scope of the appended claims.

Testing Methods

MEASUREMENT OF pH—A standard pH meter is used to measure pH. It is believed that pH testing methods and apparatuses are so standardized, that one skilled in the art would understand how to reliably test the pH of a given solution. Typically the pH meter is calibrated to the desired pH range (e.g., from pH 6 to pH 10) according to the manufacturer's instructions prior to use.

The pH should generally be measured at the dilution of actual use as recommended by the detergent manufacturer. However, because such dilutions vary widely, a standard dilution herein is a ratio of detergent to water of 1:350 by weight. The pH is taken at 20° C. Unless otherwise specifically stated, the pH is measured neat.

SUDS TESTING PROTOCOL: Foam volume and foam mileage are measured by FOAMSCAN instrument manufactured by Teclis I.T.-Concept, Longessaigne, France. The experiment is run at 25.0° C. (±0.5° C.). A cleaning solution (100 mL of correspondent concentration in ppm unit) to be tested is prepared at pH 10 or pH 8 and various water-hardness conditions (Deionized (DI) Water, 4 gpg, 8 gpg, 12 gpg, 16 gpg). The cleaning solution contains 25 ppm Technical Body Soil ("TBS"; consisting of 15 wt. % coconut oil, 15 wt. % oleic acid, 15 wt. % paraffin oil, 15 wt. % olive oil, 15 wt. % cottonseed oil, 5 wt. % squalene, 5 wt. % cholesterol, 5 wt % myristic acid, 5 wt. % palmitic acid, and 5 wt. % stearic acid). The cleaning solution is mixed and aged at 60° C. for an hour and is placed into the FOAMSCAN sample chamber, a 1000-mL cylindrical transparent plastic cell. The solution is stirred for five minutes and continuously monitored for ten minutes to measure the time course of the suds height, via two CCD cameras. The suds volume recorded at the end of stifling is defined as the suds volume generated. The suds mileage is monitored by the time course of the suds height over 10 minutes. The final suds volume at the end of the 10 minutes is reported.

MEASUREMENT OF MICELLAR LIFETIME ($\tau_2$): The micellar stability of a surfactant system is measured by Stopped Flow Conductimetry. The experiment is run at 25.0° C. (±0.5° C.). A composition (1) comprising the surfactant system to be tested (concentration 600 ppm) is prepared in DI water with 50 ppm TBS (described in the Suds Test Method above), at pH 10 or pH 8. A composition (2) comprising DI water having a hardness of 8 gpg or 16 gpg is prepared at the same pH. Compositions 1 and 2 are pumped and mixed together, in a 1:1 volumetric ratio (FC-20 cuvette; 50 μL, mixing time 2 ms), using the syringes of a SFM-20 stopped-flow fluid-mixing apparatus, supplied by the Bio-Logic SAS Company, CLAIX, France. The conductivity of the solution is monitored by a MCS-200 Impedance Spectrometer from Bio-Logic SAS. The $\tau_2$ value is defined as the time required to reach a new equilibrium, as determined by curve-fit software BKMCS (version #1) from the Bio-Logic SAS company.

PREPARATION OF HARDNESS SOLUTION: Hardness is indicated by a calculation where both calcium and magnesium values are reported as mg/L (ppm), in which 2.5[Ca]+4.12[Mg] equals hardness in mg/L. The unit "grains per gallon" (gpg) is defined as 1 grain (64.8 mg) of calcium carbonate per U.S. gallon (3.79 L), or 17.118 ppm. Thus, 1 gpg is equivalent to 17.118 ppm of the Calcium and Magnesium solution at a 3:1 molar ratio of calcium to magnesium.

MEASUREMENT OF THE CRITICAL MICELLE FORMATION CONCENTRATION (CMC): CMC measurements are conducted by a measurement of a surface tension measure as a function of surfactant concentration according to "Surfactant: A Practical Handbook," K. Robert Lange ed., Hanser Publishers, Munich (1999), pp. 16-17. A 5000-ppm stock solution of the samples is prepared for the analysis on a Kruss K100 Tensiometer (Kruss USA, Charlotte, N.C.). The hardness level and pH are adjusted using corresponding stock solutions of artificial hardness and an NaOH solution. The concentration series is generated automatically with a computer-controlled Dosimat, so that only a surfactant stock solution needs to be prepared. Measurements of surface tension at the air-water interface are carried out at twelve surfactant concentrations. The samples are analyzed at pH 8 and pH 10 for hardness values of 4 gpg and 8 gpg, all measurements being taken at 25.0° C. (±0.5° C.). The CMC data are analyzed by plotting increase in surface tension with respect to dilution by using the "CMC Add-In" of the Lab Desk software from Kruss. The CMC is defined as the surfactant concentration at the breakpoint in the titration curve.

MARANGONI EFFECT (EYE") MEASUREMENT: The Marangoni Effect quantifies the origin of foam film stability. Dynamic interfacial rheology is measured by a DSA100 (Kruss USA, Charlotte, N.C.) instrument equipped with an Oscillating Drop Module (ODM). The measurement is based on monitoring oscillating pendent drop shape with a CCD camera. The dynamic changes in the surface area and the interfacial tension (air-liquid interface) of the pendent drop from oscilating at equal periods, were recorded. A delay of dynamic interfacial tension change to dynamic surface area change is expressed as a phase angle $\Phi$ having units of time (seconds). From the measured phase angle, the Elastic Modulus (E') and Viscous Modulus (E") are calculated. The Marangoni Effect EYE" is computed from the relationship, $E'/E"=\cot \Phi$. At various surfactant levels, measurements are conducted at pH 10 and 4 gpg hardness in a base matrix of 300 ppm LAS (detergent measurements only) or 2000 ppm fatty acid (bar soap measurements only); 2300 ppm $Na_2SO_4$, and 25 ppm TBS (described above). The pH-switchable cosurfactants are added on the top of the base matrix to assess their impact on foam-film stability. The ODM operation is conducted with a period time of 2 seconds and an oscillation amplitude of 0.1 or 0.5.

MEASUREMENT OF $pK_a$ FROM pH TITRATION: To determine $pK_a$ values, a pH titration is conducted using a TitroLine pH titrator (SCHOTT Instruments Mainz, Germany). The pH meter is calibrated at pH 4, pH 7, and pH 10 before every titration, while maintaining the same magnet spin rate during calibration used during titration. A 50-mL test solution is prepared containing 30000 ppm of an additional surfactant (such as LAS, lauric acid, or another sudsing surfactant) and 2500 ppm of the pH-switchable surfactant. The solution was titrated with 0.1 M aqueous HCl to acidify the solution to a pH below 3, ensuring complete protonation of the surfactants. The solution is titrated with 0.1 M NaOH until the pH reaches 11 or greater. The pH and the volume of NaOH solution at each titration point are recorded. Based on the protonation equilibrium for the amine groups of the pH-switchable surfactants, the $pK_a$ is equal to the pH at the half equivalent point determined from the titration.

Example 1

General Synthesis of pH-Switchable Co-Surfactants

To a solution of 3-bromo-N,N,N-trimethylpropan-1-aminium bromide (119 g, 0.455 mol, 1.0 equiv) in ethanol (1.2 L) is added N-methyldodecan-1-amine (100 g, 0.501 mol, 1.5 equiv.) in 100 mL ethanol at room temperature over 15 minutes. The resulting solution is refluxed for 18 h, then cooled to room temperature. Solid sodium hydroxide (18.2 g, 0.455 mol, 1.0 equiv.) is added, and the reaction is stirred 2 hours at room temperature. The precipitate that forms is filtered under vacuum, and the mother liquor is concentrated to provide a white solid. The solid is dissolved in water (300 mL) and extracted 3 times with a mixture of $Et_2O$/EtOAc (1:1 mixture, 3×300 mL). The layers are separated, and the aqueous layer is collected, frozen (−20° C. freezer) and lyophilized under vacuum (48 h). The resulting 3-(dodecyl(methyl)amino)-N,N,N-trimethylpropan-1-aminium bromide material is collected as white, fluffy solid (166 g).

Based on the procedure above, and substituting the appropriate amines and/or alkylating agent, the following compounds are prepared:

3-(octylamino)-N,N,N-trimethylpropan-1-aminium bromide;
3-(methyl(octyl)amino)-N,N,N-trimethylpropan-1-aminium bromide;
4-(methyl(octyl)amino)-N,N,N-trimethylbutan-1-aminium bromide;
6-(methyl(octyl)amino)-N,N,N-trimethylhexan-1-aminium bromide;
3-(decyl(methyl)amino)-N,N,N-trimethylpropan-1-aminium bromide;
3-(decylamino)-N,N,N-trimethylpropan-1-aminium bromide;
4-(decyl(methyl)amino)-N,N,N-trimethylbutan-1-aminium bromide;
6-(decyl(methyl)amino)-N,N,N-trimethylhexan-1-aminium bromide;
3-(dodecylamino)-N,N,N-trimethylpropan-1-aminium bromide;
3-(dodecyl(methyl)amino)-N,N,N-trimethylpropan-1-aminium bromide;
4-(dodecyl(methyl)amino)-N,N,N-trimethylbutan-1-aminium bromide;
6-(dodecyl(methyl)amino)-N,N,N-trimethylhexan-1-aminium bromide;
3-(methyl(tetradecyl)amino)-N,N,N-trimethylpropan-1-aminium bromide;
3-(tetradecylamino)-N,N,N-trimethylpropan-1-aminium bromide;
4-(methyl(tetradecyl)amino)-N,N,N-trimethylbutan-1-aminium bromide;
6-(methyl(tetradecyl)amino)-N,N,N-trimethylhexan-1-aminium bromide;
3-(dodecyl(propyl)amino)-N,N,N-trimethylpropan-1-aminium bromide;
4-(dodecyl(propyl)amino-N,N,N-trimethylbutan-1-aminium bromide;
5-(dodecyl(propyl)amino)-N,N,N-trimethylpentan-1-aminium bromide;
3-(dodecyl(isobutyl)amino)-N,N,N-trimethylpropan-1-aminium bromide;
4-(dodecyl(isobutyl)amino)-N,N,N-trimethylbutan-1-aminium bromide;
5-(dodecyl(isobutyl)amino)-N,N,N-trimethylpentan-1-aminium bromide; and
3-(dodecyl(propyl)amino)-N,N,N-trimethylpropan-1-aminium bromide.

Example 2

Modified Synthesis of pH-Switchable Co-Surfactants

To a solution of propylamine (5.5 mL, 0.067 mol) in EtOH (100 mL) is added 3-bromo-N,N,N-trimethylpropan-1- aminium bromide (5.0 g, 0.0191 mol) portionwise at 0° C. over 20 minutes. The solution is warmed to room temperature and then refluxed for 4 hours. The solution is cooled to room temperature, and the solvent is removed via rotary evaporator to provide the crude di-bromo salt (5.69 g, 0.0179 mol). The salt is dissolved in MeOH (200 mL) and NaOH is added portionwise (0.717 g, 0.0179 mol) in MeOH (50 mL) over 30 minutes at room temperature. The solution is stirred an additional 2 hours at room temperature after addition is complete and then the solvent is removed via rotary evaporator. The residue is stirred with $CH_3CN$ (150 mL) for 30 minutes and the solids filtered off. The filtrate is concentrated via rotary evaporation and the residue is pumped on 24 h under vacuum to provide the 3-(propylamino)-N,N,N-trimethylpropan-1-aminium bromide (4.07 g, 0.017 mol), which is used without further purification. The 3-(propylamino)-N,N,N-trimethylpropan-1-aminium bromide (4.07 g, 0.017 mol) is dissolved in EtOH (100 mL) and 1-bromododecane (4.55 mL, 0.019 mol) is added dropwise over 15 minutes. The reaction is refluxed 24 hours, cooled to room temperature, and solid NaOH (0.68 g, 0.017 mol) is added. The reaction is stirred 2 hours at room temperature, and then the solids are filtered off. The filtrate is concentrated to give a white solid. The solid is dissolved in water (200 mL) and extracted with EtOAc (3×150 mL). The organic layers are combined and discarded, and the aqueous layer is frozen and lyophilized under vacuum for 48 hours to provide 3-(dodecyl(propyl)amino)-N,N,N-trimethylpropan-1-aminium bromide as a white solid (5.29 g, 0.013 mol).

Using the above procedure and the appropriate amines and bromoalkyl trimethyl ammonium salts, the following compounds are made:
4-(dodecyl(propyl)amino-N,N,N-trimethylbutan-1-aminium bromide;
5-(dodecyl(propyl)amino)-N,N,N-trimethylpentan-1-aminium bromide;
3-(dodecyl(isobutyl)amino)-N,N,N-trimethylpropan-1-aminium bromide;
4-(dodecyl(isobutyl)amino)-N,N,N-trimethylbutan-1-aminium bromide; and
5-(dodecyl(isobutyl)amino)-N,N,N-trimethylpentan-1-aminium bromide.

Example 3

Additional Synthesis Method of pH-Switchable Co-Surfactants

To a solution of N-(1-dodecyl)-1,3-propane diamine (CAS#5538-95-4) (100 g, 0.413 mol) in MeOH (1.5 L) was added formaldehyde (3.5 equiv, 1.45 mol), and the solution is refluxed for 2 hours. The solution is cooled to room temperature and 5% Pd/C catalyst (2.0 grams) is added. The solution is sparged with $N_2$ and evacuated. Hydrogen gas is then introduced (1 atm, 760 torr) and the reaction is stirred overnight at room temperature. Excess hydrogen is evacuated off, and the reaction is filtered through Celite 545 to remove the catalyst. The filtrate is concentrated to provide N'-(1-dodecyl)-N',N'',N''-trimethylpropane-1,3-diamine, which is used immediately in the next step. The trimethyl diamine is dissolved in acetone (1.2 L) and cooled to 0° C. Methyl chloride (20.65 grams, 1.0 equiv., 0.413 mol) is added dropwise over 1 hour, and the reaction is warmed to room temperature and stirred 24 hr. The solvent is removed by rotary evaporator, and the product was triturated with hexanes and filtered to provide 3-(dodecyl(methyl)amino)-N,N,N-trimethylpropan-1-aminium chloride as a white solid.

Example 4

Characterizations of 3-(dodecyl(methyl)amino)-N,N, N-trimethylpropan-1-aminium bromide ("DIAMINE") pH-Switchable Co-Surfactant To demonstrate the effectiveness of pH-switchable co-surfactants described herein, test solutions are prepared and foam volume and micellar lifetime are measured on the test solutions using the test protocols described above. As a control, a solution of LAS (linear alkyl benzene sulfonate) is prepared containing 300 ppm LAS and 25 ppm TBS (described above) in water having a hardness of 4 gpg. As a further basis for comparison, a second solution is prepared containing 300 ppm LAS, 25 ppm TBS, and 25 ppm of KDB co-surfactant in water having a hardness of 4 gpg. The KDB co-surfactant is a quaternary amine, dodecyl-(2-hydroxyethyl)-dimethyl ammonium bromide. As an additional basis for comparison, a third solution is prepared containing 300 ppm LAS, 25 ppm TBS, and 25 ppm of 3-(dodecylamino)-N,N,N-trimethylpropan-1-aminium bromide ("QUAT"), listed as molecule (21) in TABLE 1 above where group $R^2$ is a hydrogen atom, in water having a hardness of 4 gpg. An inventive test examples is prepared containing 300 ppm LAS, 25 ppm TBS, and 25 ppm of 3-(dodecyl(methyl)amino)-N, N,N-trimethylpropan-1-aminium bromide ("DIAMINE"), listed as molecule (3) in TABLE 1, and as prepared according to the methods described in Example 1 or 2 above, in water having a hardness of 4 gpg. Foam volumes measured at a hypothetical washing pH of 10.0 and a hypothetical rinsing pH of 8.0, $pK_a$ values measured for diamine surfactants in the presence of LAS are shown in TABLE 2, micellar lifetimes at the same pH values are shown in TABLE 3, Marangoni force values are shown in TABLE 4, and critical micellar concentrations (CMC) are shown in TABLE 5.

TABLE 2

| Composition | Foam Volume pH 10.0 (wash) | Foam Volume pH 8.0 (rinse) | Change of Foam Volume (rinse vs. wash) | $pK_a$ |
|---|---|---|---|---|
| LAS Only (Comparative) | 186 mL | 183 mL | −2% | — |
| LAS + KDB (Comparative) | 180 mL | 177 mL | −2% | — |
| LAS + QUAT (Comparative) | 95 mL | 115 mL | +17% | 10.0 |
| LAS + DIAMINE (Inventive) | 175 mL | 105 mL | −40% | 9.0 |

TABLE 3

| Composition | Micellar Lifetime ($\tau_2$) pH 10.0 (wash) | Micellar Lifetime ($\tau_2$) pH 8.0 (rinse) | Change of $\tau_2$ (rinse-wash) |
|---|---|---|---|
| LAS Only (Comparative) | 18.0 s | 17.7 s | −2% |
| LAS + KDB (Comparative) | 17.1 s | 15.8 s | −7% |
| LAS + QUAT (Comparative) | 28.0 s | 26.5 s | −5% |
| LAS + DIAMINE (Inventive) | 14.4 s | 17.6 s | +22% |

TABLE 4

| Composition | Marangoni Effect (E'/E") at pH 10 |
|---|---|
| LAS Only (Comparative) | 2.0 |
| LAS + KDB (Comparative) | 3.6 |
| LAS + QUAT (Comparative) | 1.5 |
| LAS + DIAMINE (Inventive) | 5.1 |

TABLE 5

| | CMC (ppm) | |
|---|---|---|
| Composition | pH 10 | pH 8 |
| KDB (Comparative) | 43 | 48 |
| QUAT (Comparative) | 75 | 82 |
| DIAMINE (Inventive) | 42 | 321 |

From the above test solutions, it can be seen that the inventive pH-switchable co-surfactant provides a substantially greater reduction of suds volume at rinsing pH, compared to the suds volume at washing pH, than any of the comparative examples.

The benefits of the pH-switchable co-surfactant according to embodiments herein are further evident from comparisons with ingredients in personal bar soaps. The suds characteristics of inventive 2.5 wt. % DIAMINE in combination with lauric acid (2000 ppm) were compared against an identical solution containing lauric acid only. The results are shown in TABLE 6.

TABLE 6

| | pH 10.0 (wash) | | | pH 8.0 (rinse) |
|---|---|---|---|---|
| | Foam Volume | τ2 | E'/E" | Foam Volume |
| Lauric Acid (comparative) | 80 mL | 39 ms | 1.5 | 222 mL |
| Lauric Acid + DIAMINE (Inventive) | 218 mL | 35 ms | 3.3 | 58 mL |
| Change | +173% | −10% | +120% | −75% |

The results in TABLE 6 illustrate a remarkable suds-boosting effect of the inventive pH-switchable co-surfactant at washing pH, combined with a dramatic suppression of suds benefit at rinsing pH.

Characteristics of the pH-switchable co-surfactant also vary with water hardness, as shown in TABLE 7.

TABLE 7

| | | Lather Volume (mL) of test solutions in water with varying degrees of hardness | | | | |
|---|---|---|---|---|---|---|
| | | DI Water | 4 gpg | 8 gpg | 12 gpg | 16 gpg |
| Sodium Laurate (comparative) | pH 10.0 (wash) | 220 | 215 | 175 | 0 | 0 |
| | pH 8.0 (rinse) | 170 | 60 | 0 | 0 | 0 |
| | Change | −23% | −72% | −100% | — | — |
| Sodium Laurate + DIAMINE (inventive) | pH 10.0 (wash) | 205 | 200 | 195 | 180 | 160 |
| | pH 8.0 (rinse) | 220 | 215 | 215 | 95 | 40 |
| | Change | +7.3% | +7.5% | +10.3% | −47% | −75% |

The results in TABLE 7 show that the pH-switchable cosurfactant provides a high level of suds at the washing pH, even when the washing water is extremely hard. At the rinse minic high hardness conditions, suds at the rinsing pH are significantly reduced over the suds at the washing pH.

In TABLE 8, suds volume is compared with respect to amount of DIAMINE in a solution containing 2000 ppm of Soap Noodles (20 wt. % Palm Kernel Oil (PKO), 80 wt. % tallow). DIAMINE levels of from 50 ppm to 200 ppm are compared against a test solution containing no DIAMINE.

TABLE 8

| | | Amount of DIAMINE in test solution containing 2000 ppm Soap Noodles | | | |
|---|---|---|---|---|---|
| | | 0 ppm (comparative) | 50 ppm | 100 ppm | 200 ppm |
| Water with 8 gpg hardness | pH 10.0 (wash) | 185 | 185 | 184 | 165 |
| | pH 8.0 (rinse) | 201 | 0 | 0 | 0 |
| | Change | +8.6% | −100% | −100% | −100% |

The results in TABLE 8 demonstrate complete elimination of rinsing lather in the test solutions with 8 gpg hardness.

Examples 5-12

Powder Laundry Detergent Compositions

Exemplary cleaning compositions containing a pH-switchable cosurfactant and formulated as powder laundry detergent compositions according to embodiments described herein are provided in TABLES 9 and 10. In the exemplary compositions, "DIAMINE" refers to a pH-switchable cosurfactant prepared according to the synthesis methods described in Examples 1-3.

TABLE 9

| | Concentration (Weight percent) | | | |
|---|---|---|---|---|
| Component | Example 5 | Example 6 | Example 7 | Example 8 |
| Sodium LAS | 12 | 14 | 8 | 5 |
| Sodium AS | 2 | 1 | — | — |
| Sodium AE$_3$S | 2 | — | — | — |
| Sodium AE$_1$S | — | 2 | 4 | 5 |
| DIAMINE | 0.7 | 0.8 | 0.6 | 0.4 |
| Non ionic surfactant | 0.3 | 0.3 | — | — |
| Zeolite | 4 | 3 | — | — |
| Na$_2$CO$_3$ | 32 | 28 | 35 | 34 |
| Silicate | 4 | 4 | 7 | 8 |
| Polymers | 12 | 11 | 15 | 14 |
| Enzyme | 2 | 1 | 2.5 | 2.6 |
| Bleach system | 6 | 5 | 8 | 10 |
| Sodium sulfate | 15 | 18 | 12 | 15 |
| Water and miscellaneous | Balance to 100% | Balance to 100% | Balance to 100% | Balance to 100% |

TABLE 10

| | Concentration (Weight percents) | | | |
|---|---|---|---|---|
| Component | Example 9 | Example 10 | Example 11 | Example 12 |
| Sodium LAS | 12 | 14 | 8 | 7 |
| Sodium AS | 2 | — | — | — |
| Sodium AE$_3$S | — | 1 | — | 3 |
| Sodium AE$_1$S | — | 1 | — | 3 |
| STPP | 10 | 6 | 8 | 7 |
| DIAMINE | 0.7 | 0.8 | 0.3 | 0.3 |
| Non ionic surfactant | 0.3 | 0.3 | — | — |

TABLE 10-continued

| Component | Concentration (Weight percents) | | | |
|---|---|---|---|---|
| | Example 9 | Example 10 | Example 11 | Example 12 |
| Zeolite | 4 | 3 | — | — |
| Sodium carbonate | 22 | 20 | 22 | 27 |
| Silicate | 3 | 4 | 7 | 8 |
| Carboxy Methyl Cellulose | 0.8 | 0.7 | 0.8 | 1 |
| Polymers | 11 | 10 | 14 | 13 |
| Enzyme | 2 | 1.5 | 2.5 | 2.6 |
| Bleach system | 6 | 5 | 8 | 10 |
| $Na_2SO_4$ | 15 | 24 | 12 | 15 |
| Water and miscellaneous | Balance to 100% | Balance to 100% | Balance to 100% | Balance to 100% |

Examples 13-23

Liquid Laundry Detergent Compositions

Exemplary cleaning compositions containing a pH-switchable cosurfactant and formulated as liquid laundry detergent compositions according to embodiments described herein are provided in TABLES 11 and 12. In the exemplary compositions, "DIAMINE" refers to a pH-switchable cosurfactant prepared according to the synthesis methods described in Examples 1-3. The compositions of Examples 13-23 each are formulated to have a washing pH of from about 9.5 to about 10.5.

TABLE 11

| Component | Concentration (Weight Percent) | | | | |
|---|---|---|---|---|---|
| | Example 13 | Example 14 | Example 15 | Example 16 | Example 17 |
| LAS | 18.0 | — | 6.0 | — | — |
| $C_{12}$-$C_{15}$ $AE_{1.8}S$ | — | 2.0 | 8.0 | 11.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethylamine oxide | — | — | — | — | 2.0 |
| $C_{12}$-$C_{15}$ AS | — | 17.0 | — | 7.0 | 8.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 11.0 | 11.0 | 4.0 | 4.0 | 3.0 |
| Citric acid (anhydrous) | 5.0 | 1.0 | 3.0 | 3.0 | 2.0 |
| DIAMINE | 1.0 | 1.0 | 1.0 | 1.0 | 0.5 |
| Monoethanolamine | 11.0 | 8.0 | 5.0 | 5.0 | 2.0 |
| Sodium hydroxide | 1.0 | 1.0 | 2.5 | 1.0 | 1.5 |
| Percarbonate | — | 3.5 | — | 2.5 | — |
| Propanediol | 12.7 | 14.5 | 13.1 | 10. | 8.0 |
| Ethanol | 1.8 | 1.8 | 4.7 | 5.4 | 1.0 |
| Pectin Lyase | — | — | — | 0.005 | — |
| Amylase | — | 0.002 | — | — | — |
| Cellulase | — | — | 0.0002 | — | 0.0001 |
| Lipase | 0.1 | — | 0.1 | — | 0.1 |
| Protease | 0.1 | 0.6 | 0.12 | 1.0 | 0.4 |
| Boric acid | 2.4 | 2.4 | 2.8 | 2.8 | 2.4 |
| Sodium xylene sulfonate | — | — | 3.0 | — | — |
| 2-butyl-octanol | 0.03 | 0.04 | 0.04 | 0.03 | 0.03 |
| Brightener | 0.18 | 0.10 | 0.11 | — | — |
| Perfume and/or dye and/or water | Balance to 100% | Balance to 100% | Balance to 100% | Balance to 100% | Balance to 100% |

TABLE 12

| Component | Concentration (Weight Percent) | | | | | |
|---|---|---|---|---|---|---|
| | Example 18 | Example 19 | Example 20 | Example 21 | Example 22 | Example 23 |
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| DIAMINE | 1.5 | 1.5 | 0.5 | 1.2 | 1.4 | 1.2 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| Na Culmene Sulfonate | 4.0 | 4.0 | 1.0 | 3.0 | 1.2 | — |
| Borate | 0.6 | 0.6 | — | 3.0 | 2.0 | 3.0 |
| Na hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2-Propanediol | 3.0 | 3.0 | 2.0 | 8.0 | 8.0 | 5.0 |
| Monoethanolamine | 3.0 | 3.0 | 1.5 | 1.0 | 2.5 | 1.0 |
| Protease | 0.06 | 0.08 | 0.02 | 0.06 | 0.10 | 0.04 |
| Lipase | — | — | — | 0.002 | — | — |

TABLE 12-continued

| Component | Example 18 | Example 19 | Example 20 | Example 21 | Example 22 | Example 23 |
|---|---|---|---|---|---|---|
| Amylase | — | — | — | — | 0.002 | — |
| Cellulase | — | — | — | — | — | 0.0001 |
| Pectin Lyase | 0.005 | 0.005 | — | — | — | — |
| Silicone antifoam | 0.04 | 0.04 | 0.02 | 0.1 | 0.1 | 0.1 |
| Perfume/dye, and/or water | Balance to 100% | Balance to 100% | Balance to 100% | Balance to 100% | Balance to 100% | Balance to 100% |

Examples 24-29

Liquid Dishwashing Compositions

Exemplary cleaning compositions containing a pH-switchable cosurfactant and formulated as liquid dishwashing compositions according to embodiments described herein are provided in TABLE 13. In the exemplary compositions, "DIAMINE" refers to a pH-switchable cosurfactant prepared according to the synthesis methods described in Examples 1-3.

TABLE 13

| Component | Example 24 | Example 25 | Example 26 | Example 27 | Example 28 | Example 29 |
|---|---|---|---|---|---|---|
| $C_{12}$-$C_{15}AE_{1.8}S$ | 30.0 | 28.0 | 30.0 | — | 15.0 | 15.0 |
| LAS | — | — | — | 5.0 | 15.0 | 12.0 |
| Paraffin sulfonate | — | — | — | 20.0 | — | — |
| $C_{10}$-$C_{18}$ alkyl dimethyl amine oxide | 5.0 | 3.0 | 7.0 | — | 3.0- | — |
| Betaine | 2.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| Tri-sodium citrate dihydrate | 0.25 | — | — | 0.7 | — | — |
| DIAMINE | 2.0 | 5.0 | 3.0 | 1.0 | 2.0 | 2.0 |
| $MgCl_2$ | 0.25 | — | — | 1.0 | — | — |
| Protease | 0.02 | 0.01 | 0.02 | 0.01 | 0.02 | 0.05 |
| Amylase | 0.001 | — | — | 0.002 | — | 0.001 |
| Sodium cumene sulfonate | — | — | — | 2.0 | 1.5 | 3.0 |
| Perfume/dye and/or water | Balance to 100% | Balance to 100% | Balance to 100% | Balance to 100% | Balance to 100% | Balance to 100% |

Examples 30-39

Personal Bar Soap Compositions

Exemplary cleaning compositions containing a pH-switchable cosurfactant and formulated as personal bar soap compositions according to embodiments described herein are provided in TABLES 14 and 15. In the exemplary compositions, "DIAMINE" refers to a pH-switchable cosurfactant prepared according to the synthesis methods described in Examples 1-3. To test pH of the soap compositions in solid form, the soap composition is first dissolved in distilled water to form an aqueous solution of a concentration of 10%. The pH (25° C.) of this aqueous solution is then presumed to be representative of the bar soap.

TABLE 14

| Component | Example 30 | Example 31 | Example 32 | Example 33 | Example 34 |
|---|---|---|---|---|---|
| Soap noodle[1] | 96.5 | 92.4 | 80.1 | 96.0 | 95.8 |
| $TiO_2$ | 0.5 | 0.5 | 0.5 | 0.5 | 0.5 |
| Perfume | 0.5 | 0.5 | 0.5 | 0.5 | 0.5 |
| Brightener | 0.04 | 0.04 | 0.04 | 0.04 | 0.04 |

TABLE 14-continued

| Component | Concentration (Weight Percent) | | | | |
|---|---|---|---|---|---|
| | Example 30 | Example 31 | Example 32 | Example 33 | Example 34 |
| DIAMINE | 2.5 | 2.3 | 2.0 | 2.3 | 2.2.0 |
| $Na_2CO_3$ | — | 3.8 | 16.4 | — | — |
| NaOH | — | — | — | 0.25 | 0.50 |
| Water | Balance to 100% | Balance to 100% | Balance to 100% | Balance to 100% | Balance to 100% |
| pH (10% sol) | 9.96 | 10.79 | 11.05 | 10.92 | 11.74 |

[1] 20 wt. % Palm kernel oil, 80 wt. % tallow

TABLE 15

| Component | Concentration (Weight Percent) | | | | |
|---|---|---|---|---|---|
| | Example 35 | Example 36 | Example 37 | Example 38 | Example 39 |
| Soap noodle[1] | 96.0 | 95.8 | 94.1 | 94.05 | 94.05 |
| $TiO_2$ | 0.5 | 0.5 | 0.5 | 0.5 | 0.5 |
| Perfume | 0.5 | 0.5 | 0.5 | 0.5 | 0.5 |
| Brightener | 0.04 | 0.04 | 0.04 | 0.04 | 0.04 |
| $Na_2CO_3$ | — | — | 2 | 2 | 2 |
| DIAMINE | 2.5 | 2.3 | 2.0 | 2.0 | 2.0 |
| ZnO | — | — | — | 0.05 | — |
| $ZnCO_3$ | — | — | — | — | 0.05 |
| Water | Balance | Balance | Balance | Balance | Balance |
| pH (10% sol) | <10.7 | | | >10.7 | |

[1] 20 wt. % Palm kernel oil, 80 wt. % tallow

Examples 40-43

Bar Fabric Cleaning Compositions

Exemplary cleaning compositions containing a pH-switchable cosurfactant and formulated as laundry bar compositions according to embodiments described herein are provided in TABLE 16. In the exemplary compositions, "DIAMINE" refers to a pH-switchable cosurfactant prepared according to the synthesis methods described in Examples 1-3. To test pH of the laundry bar compositions in solid form, the laundry bar composition is first dissolved in distilled water to form an aqueous solution of a concentration of 10%. The pH (25° C.) of this aqueous solution is then presumed to be representative of the bar soap.

TABLE 16

| Component | Concentration (Weight Percent) | | | |
|---|---|---|---|---|
| | Example 40 | Example 41 | Example 42 | Example 43 |
| LAS | 10.0 | 10.0 | 9.5 | 9.7 |
| $C_{12}$-$C_{16}$ AS, Sodium Salt | 20.0 | 19.2 | 20.0 | 20.0 |
| $C_{12}$-$C_{14}$ N-methyl glucamide | 3.5 | 4.0 | 4.0 | 3.5 |
| DIAMINE | 1.5 | 1.8 | 1.5 | 1.8 |
| Sodium Carbonate | 25.0 | 25.0 | 25.0 | 25.0 |
| Sodium Tripolyphosphate | 7.0 | 7.0 | 7.0 | 7.0 |
| Zeolite A (0.1 μm-10 μm) | 5.0 | 5.0 | 5.0 | 5.0 |
| Carbyxymethylcellulose | 0.2 | 0.2 | 0.2 | 0.2 |
| Polyacrylate (MW 1400) | 0.2 | 0.2 | 0.2 | 0.2 |
| Coconut Monoethanolamine | 5.0 | 5.0 | 5.0 | 5.0 |
| Brightener, perfume | 0.2 | 0.2 | 0.2 | 0.2 |
| $CaSO_4$ | 1.0 | 1.0 | 1.0 | 1.0 |
| $MgSO_4$ | 1.0 | 1.0 | 1.0 | 1.0 |
| Protease | 0.3 | 0.1 | 0.5 | 0.12 |
| Amylase | 0.01 | 0.02 | 0.002 | 0.005 |
| Cellulase | — | — | 0.0002 | — |
| Water | 3.7 | 3.7 | 3.7 | 3.7 |
| Perfume | 0.3 | 0.2 | 0.3 | 0.3 |
| Filler[1] | Balance to 100% | Balance to 100% | Balance to 100% | Balance to 100% |

[1] May be selected from convenient materials such as $CaCO_3$, talc, clay, silicates, and the like.

Unless otherwise defined, all technical and scientific terms used herein have the same meaning as commonly understood by one of ordinary skill in the art to which the invention belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All percentages, parts and ratios are based upon the total weight of the compositions, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Though particular embodiments have been illustrated and described, it would be obvious to those skilled in the art that various other changes and modifications can be made without departing from the spirit and scope of the appended claims. It is therefore intended to cover in the appended claims all such changes and modifications.

What is claimed is:

1. A cleaning composition comprising:
   from about 0.01 wt. % to about 70 wt. %, based on the total weight of the cleaning composition, of a pH-switchable sudsing system; and
   from about 0.0001 wt. % to about 99.99 wt. %, based on the total weight of the cleaning composition, of a cleansing system,
   wherein the pH-switchable sudsing system comprises:
   from about 0.05 wt. % to 99.99 wt. %, based on the total weight of the pH-switchable sudsing system, of a primary sudsing agent; and
   from 0.01 wt. % to about 15 wt. %, based on the total weight of the pH-switchable sudsing system, of a pH-switchable co-surfactant or a mixture of pH-switchable co-surfactants, each pH switchable co-surfactant being selected from compounds having formula (I):

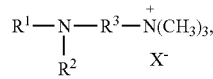

(I)

where:
   $R^1$ is a linear or branched $C_8$ to $C_{16}$ hydrocarbyl,
   $R^2$ is a linear or branched $C_1$ to $C_3$ hydrocarbyl,
   $R^3$ is a linear or branched $C_3$ to $C_6$ hydrocarbylene, and
   X is a counteranion.

2. The cleaning composition of claim 1, wherein the primary sudsing agent is selected from the group consisting of anionic surfactants, free fatty acids, nonionic surfactants, amphoteric surfactants, zwitterionic surfactants, and combinations thereof.

3. The cleaning composition of claim 1, wherein the pH-switchable co-surfactant and the primary sudsing agent are chosen such that the pH-switchable co-surfactant has a $pK_a$ of from about 8.0 to about 10.0, whereby the pH-switchable co-surfactant boosts suds formation in an aqueous wash solution at a washing pH greater than said $pK_a$.

4. The cleaning composition of claim 3, wherein the cleansing system further comprises a pH control system, whereby during dilution in the aqueous wash solution and during washing, the pH control system maintains the pH of the aqueous wash solution greater than the $pK_a$ of the pH-switchable co-surfactant.

5. The cleaning composition of claim 1, wherein the pH-switchable co-surfactant and the primary sudsing agent are chosen such that the pH-switchable co-surfactant has a $pK_a$ of from about 8.0 to about 10.0, whereby the pH-switchable co-surfactant suppresses suds in the aqueous wash solution at a rinsing pH less than said $pK_a$.

6. The cleaning composition of claim 1, wherein:
   $R^1$ is selected from the group consisting of decyl, dodecyl, and tetradecyl;
   $R^2$ is selected from the group consisting of methyl, ethyl, and n-propyl; and
   $R^3$ is selected from the group consisting of 1,3-propanediyl, 1,4-butanediyl, and 1,5-pentanediyl.

7. The cleaning composition of claim 6, wherein $R^1$ is dodecyl, $R^2$ is methyl, and $R^3$ is 1,3-propanediyl.

8. The cleaning composition of claim 1, wherein the weight ratio of the primary sudsing agent to the pH-switchable co-surfactant in the cleaning composition is from about 6:1 to about 50:1.

9. The cleaning composition of claim 1, wherein the cleaning composition is a solid or liquid laundry detergent, laundry bar or a liquid hand dishwashing detergent.

10. The cleaning composition of claim 9, wherein the primary sudsing agent is a sudsing surfactant selected from the group consisting of anionic surfactants, nonionic surfactants, amphoteric surfactants, zwitterionic surfactants, and combinations thereof.

11. The cleaning composition of claim 9, wherein the primary sudsing agent comprises at least one surfactant selected from the group consisting of linear alkyl benzene sulfonates, alkyl sulfates, alkyl alkoxylated sulfates, betaines, alkyl amine oxides, and mixtures thereof.

12. The cleaning composition of claim 9, wherein the pH-switchable sudsing system comprises:
   from about 5 wt. % to about 99 wt. % of the primary sudsing agent; and
   from about 1% to about 10% of the pH switchable surfactant,
   wherein the primary sudsing agent is selected from the group consisting of linear alkyl benzene sulfates, linear alkyl benzene sulfonates, alcohol ether sulfates, alcohol ether sulfonates, and mixtures thereof.

13. The cleaning composition of claim 9, wherein the cleansing system further comprises at least one detergent adjunct selected from the group consisting of builders, polymers, brighteners, bluing agents, chelants, enzymes, perfumes, and water.

14. The cleaning composition of claim 1, wherein the cleaning composition is a personal bar soap.

15. The cleaning composition of claim 14, wherein the primary sudsing agent comprises at least one free fatty acid.

16. The cleaning composition of claim 15, wherein the at least one free fatty acid is selected from the group consisting of pure-chain fatty acids, monoglycerides, diglycerides, triglycerides, and fatty acid-containing oils.

17. The cleaning composition of claim 14, wherein the primary sudsing agent comprises at least one free fatty acid and at least one sudsing surfactant selected from the group consisting of anionic surfactants, nonionic surfactants, amphoteric surfactants, zwitterionic surfactants, and combinations thereof.

18. The cleaning composition of claim 14, wherein the primary sudsing agent is selected from the group consisting of acyl isethionates, acyl sarcosinates, alkylglycerylether sulfonates, methylacyl taurates, paraffin sulfonates, linear alkyl benzene sulfonates, N-acyl glutamates, alkyl sulfosuccinates, alpha sulfo fatty acid esters, alkyl ether carboxylates, alkyl phosphate esters, ethoxylated alkyl phosphate esters, alpha olefin sulfonate, the alkyl ether sulfates, and mixtures thereof.

19. The cleaning composition of claim 14, wherein the cleansing system further comprises at least one conditioning ingredient selected from the group consisting of polymers, perfumes, fillers, humectants, sanitizing agents, antimicrobial agents, dyes, moisturizers, colorants, mildness aids, preservatives, clays, and water.

20. A method of hand washing a fabric, the method comprising:

A. diluting a cleaning composition according to claim 1 in water at a weight ratio of water to the cleaning composition of from about 1:150 to about 1:1000 to form a laundry liquor having a pH, wherein the pH-switchable co-surfactant of the cleaning composition has a $pK_a$;

B. hand washing a fabric in the laundry liquor;

C. maintaining pH of the laundry liquor above the $pK_a$ of the pH-switchable co-surfactant during the washing; and D. rinsing the fabric in a rinse bath having a pH less than the $pK_a$ of the pH-switchable co-surfactant.

* * * * *